United States Patent [19]
Rose et al.

[11] Patent Number: 5,861,277
[45] Date of Patent: Jan. 19, 1999

[54] METHODS AND COMPOSITIONS FOR ENHANCING THE EXPRESSION OF GENES IN PLANTS

[75] Inventors: Alan B. Rose, Davis, Calif.; Robert L. Last, Ithaca, N.Y.

[73] Assignee: Boyce Thompson Institute for Plant Research, Inc., Ithaca, N.Y.

[21] Appl. No.: 723,624

[22] Filed: Oct. 2, 1996

[51] Int. Cl.$^6$ .................................................... C12P 21/00
[52] U.S. Cl. ..................... 435/69.1; 435/41; 435/71.1; 435/127; 435/132; 435/172.1; 435/172.3; 435/410; 435/419; 435/320.1; 514/2; 514/44; 800/200; 800/205; 800/230; 800/250
[58] Field of Search ................................ 435/6, 69.1, 810, 435/41, 68.1, 71.1, 127, 132, 172.1, 172.3, 410, 419, 320.1; 436/501; 514/44, 2; 935/77, 78; 800/200, 205, 230, 250

[56] References Cited

PUBLICATIONS

Baker et al., "The 5'–region of *arabidopsis thaliana* cor 15a has cis–acting elements that confer cold–, drought–and ABA–regulated gene expression," *Plant Molecular Biology*, 24:701–713, 1994.

Berget et al., "Spliced segments at the 5' terminus of adenovirus 2 late mRNA," *Proc. Natl. Acad. Sci. USA*, 74:3171–3175, 1977.

Berlyn et al., "A gene encoding the tryptophan synthase β subunit of *arabidopsis thaliana*," *Proc. Natl. Acad. Sci. USA*, 86:4604–4608, 1989.

Chee et al., "Expression of a bean storage protein 'phaseolin minigene' in foreign plant tissues," *Gene*, 41:47–57, 1986.

Chow et al., "An amazing sequence arrangement at the 5' ends of adenovirus 2 messenger RNA," *Cell*, 12:1–8, 1977.

De Almeida et al., "Transgenic expression of two marker genes under the control of arabidopsis rbcS promoter: sequence encoding the rubisco transit peptide increase expression levels," *Mol. Gen. Genet.*, 218:78–86, 1989.

Dickey et al., "Light modulation of ferredoxin mRNA abundance requires an open reading frame," *The Plant Cell*, 6:1171–1176, 1994.

Feinbaum, R. L. and Ausubel, F. M., "Transcriptional regulation of the *arabidopis thaliana* chalcone synthase gene," *Molecular and Cellular Biology*, 8:1985–1992, 1988.

Fray et al., "Identification of unexplained DNA fragments within the T–DNA borders of the bin 19 plant transformation vector," *Plant Molecular Biology*, 25:339–342, 1994.

Gallie et al., "Posttranscriptional regulation of gene expression in plants," *Annu. Rev. Plant Mol. Biol.*, 44:77–105, 1993.

Green, M. R., "Pre–mRNA splicing," *Ann. Rev. Genet.*, 20:671–708, 1986.

Haughn, G. W. and Somerville, C., "Sulfonylurea–resistant mutants of *arabidopsis thaliana*," *Mol. Gen. Genet.*, 204:430–434, 1986.

Jeffreys, A. J. and Flavell, R. A., "The rabbit β–globin gene contains a large insert in the coding sequence," *Cell* 12, 1097–1108, 1977.

(List continued on next page.)

*Primary Examiner*—Ardin H. Marschel
*Attorney, Agent, or Firm*—Arnold, White & Durkee

[57] ABSTRACT

Disclosed are methods of increasing exogenous protein expression in a cell or a transgenic plant. Constructs, i.e., vectors, DNA fusions and polynucleotides, for use in conjunction with the methods to cause increased exogenous protein expression are also disclosed. These constructs generally include intron 1 and/or intron 2 of the PAT1 gene. Additionally disclosed are cells, including recombinant cells, and plant lines transformed with the described constructs. In particular, a cultivated, transgenic food plant, the genome of which has been augmented through the genomic introduction of a preselected exogenous protein gene not found in the genome of non-transformed parentage of the plant is described. Also described are seed, progeny and cells of the described transgenic food plant.

91 Claims, 8 Drawing Sheets

PUBLICATIONS

Kato et al., "A modified β–glucuronidase gene: sensitive detection of plant promoter activities in suspension–cultured cells of tobacco and rice," *plant Molecular Biology Reporter*, 9:333–339, 1991.

Klee et al., "Vectors for transformation of higher plants," *Biotechnology*, 3:637–642, 1985.

Kuhlemeirer et al., "Upstream sequences determine the difference in transcript abundance of pea rbcS genes," *Mol. Gen. Genet.*, 212:405–411, 1988.

Landry et al., "Arabidopsis mutants lacking phenolic sunscreens exhibit enhanced ultraviolet–B injury and oxidative damage," *Plant Physiol.*, 109:1159–1166, 1995.

Larkin et al., "Arabidopsis Glabrous1 gene requires downstream sequences for function," *The Plant Cell*, 5:1739–1748, 1993.

Last et al., "Tryptophan mutants in Arabidopsis: the consequences of duplicated tryptophan synthase β–genes," *The Plant Cell*, 3:345–358, 1991.

Last, R. L. and Fink, G. R., "Tryptophan–requiring mutants of plant *arabidopsis thaliana*," *Science*, 240:305–310, 1988.

Mascarenhas, J. P. and Hamilton, D. A., "Artifacts in the localization of GUS activity in anthers of petunia transformed with a CaMV 35S–GUS construct," *The Plant Journal*, 2:405–408, 1992.

Oard et al., "Chimeric gene expression using maize intron in cultured cells of breadwheat," *Plant Cell Reports*, 8:156–160, 1989.

Peach, C and Velten, J., "Transgene expression variability (position effect) of CAT and GUS reporter genes driven by linked divergent T–DNA promoters," *Plant Molecular Biology* 17:49–60, 1991.

Pruitt, K. D. and Last, R. L., "Expression patterns of duplicate tryptophan synthase β–genes in *arabidopsis thaliana*," *Plant Physiol.*, 102:1019–1026, 1993.

Radwanski et al., "*Arabidopsis thaliana* tryptophan synthase alpha: gene cloning, expression, and subunit interaction," *Mol. Gen. Genet.*, 248:657–667, 1995.

Ruby, S. W. and Abelson, J., "An early hierachic role of U1 small nuclear ribonuleoprotein in spliceosome assembly," *Science*, 242:1028–1035, 1988.

Sistrunk, et al., "Arabidopsis TCH3 encodes a novel $Ca^{2+}$ binding protein and shows environmentally induced and tissue–specific regulation," *The Plant Cell*, 6:1553–1565, 1994.

Sullivan, M. L. and Green, P. J., "Post–transciptional regulation of nuclear–encoded genes in higher plants: the roles of mRNA stability and translation," *Plant Molecular Biology*, 23:1091–1104, 1993.

Uknes, et al., "regulation of pathogenesis–related protein–1a gene expression in tobacco," *The Plant Cell*, 5:159–169, 1993.

Ulmasov, B. and Folk, W., "Analysis of the role of 5' and 3' flanking sequence elements upon in vivo exprssion of the plant $tRNA^{Trp}$ genes," *The Plant Cell*, 7:1723–1734, 1995.

Valvekens, et al., "*Agrobacterium tumefaciens*–mediated transformation of *arabidopsis thaliana* root explants by using kanamycin selection," *Proc. Natl. Acad. Sci. USA*, 85:5536–5540, 1988.

Vaucheret, et al., "Interest in and limits to the utilization of reporter genes for the analysis of transcriptional regulation of nitrate reductase," *Mol. Gen. Genet.*, 235:259–268, 1992.

Zhoa, J and Last, R. L., "Immunological characterization and chloroplast localization of thetryptophan biosynthetic enzymes of theflowering plant *arabidopis thaliana*," *J. Biol. Chem.*, 270, 6081–6087, 1995.

*Current Protocols in Molecular Biology*, (Suppl. 26), Ausubel et al., eds, 1993.

Chandler et al., "Two regulatory genes of the maize anthocyanin pathway are homologous: isolation of B utilizing R genomic sequences," *The Plant Cell*, 1:1175–1183, 1989.

Conkling et al., "Isolation of transcriptionally regulated root–specific genes from tobacco[1]," *Plant Physiol.*, 93:1203–1211, 1990.

Ebert et al., "Identification of an essential upstream element in the nopaline synthase promoter by stable transient assays," *Proc. Natl. Acad. Sci. USA*, 84:5745–5749, 1987.

Evans, M. J. and Scarpulla, R. C. "Introns in the 3'–untranslated region can inhibit chimeric CAT and β–galactosidase gene expression," *Gene*, 84:135–142, 1989.

Fromm et al., "An octopine synthase enhancer element directs tissue–specific expression and binds ASF–1, a factor from tobacco nuclear extracts," *The Plant Cell*, 1:977–984, 1989.

Gallie, D. R. and Young, T. E., "The regulation of gene expression in transformed maize aleurone and endosperm protoplasts[1]," *Plant Physiol.*, 106:929–939, 1994.

*Plant molecular biology manual*, Gelvin, S. B., Schilperoort, R. A. and Varma, D. P. S., eds, 1990.

Hudspeth, R. L. and Grula, J. W., "Structure and expression of the maize gene encoding the phosphoenolpyruvate carboxylase isozyme involved in $C_4$ photosynthesis," *Plant Molecular Biology*, 12:579–589, 1989.

Lawton et al., "Expression of a soybean β–conclycinin gene under the control of the cauliflower mosaic virus 35S and 19S promoters in transformed petunia tissues," *Plant Molecular Biology*, 9:315–324, 1987.

Luehrsen, K. R. and Walbot, V. "Addition of A–and U–rich sequence increases the spilcing efficiency of a deleted form of a maize intron," *Plant Molecular Biology*, 24:449–463, 1994.

Niyogi, K., "Molecular and genetic analysis of anthranilate synthase in arabidopsis thaliana," Ph.D. Dissertation, Massachusetts Institute of Technology, 1993.

Niyogi et al., "Suppressors of trp1 fluorescence identify a new arabidopsis gene, TRP4, encoding the anthranilate synthase β subunit," *The Plant Cell*, 5:1011–1027, 1993.

Odell et al., "Identification of DNA sequences required for activity of the cauliflower mosaic virus 35S promoter," *Nature*, 313:810–812, 1985.

Omirulleh et al., "Activity of a chimeric promoter with the doubled CaMV 35S enhancer element in protoplast–derived cells and transgenic plants in maize," *Plant Molecular Biology*, 21:415–428, 1993.

Rose, A. B. and Last, R. L. "Introns act post–transcriptionally to increase expression of the *arabidopsis thaliana* tryptophan pathway gene PAT1," Plant J., 11:455–464, 1997.

Rose et al, "An allelic series of blue fluorescent trp1 mutants of *arabidopsis thaliana*," *Genetics*, 145:197–205, 1997.

Sambrook, Fritsch, Maniatis, *Molecular Cloning: A Laboratory Manual*, 2nd Ed., Cold Spring Harbor Press, Cold Spring Harbor, NY, 1989.

Sullivan et al., "Isolation and characterization of a maize chlorophyll a/b binding protein gene that produces high levels of mRNA in the dark," *Mol. Gen. Genet.*, 215:431–440, 1989.

Walker et al., "DNA sequences required for anaerobic expression of the maize alcohol dehydrogenase 1 gene," *Proc. Natl. Acad. Sci. USA*, 84:6624–6628, 1987.

Wang et al., "Characterization of cis–acting elements regulating transcription form the promoter of a constitutively active rice actin gene," *Molecular and Cellular Biology*, 12:3399–3406, 1992.

Yang, N. S. and Russel, D., "Maize sucrose synthase–1 promoter directs phloem cell–specific expression of Gus gene in transgenic tobacco plants," *Proc. Natl. Acad. Sci. USA*, 87:4144–4148, 1990.

Buchman and Berg, "Comparison of Intron–Dependent and Intron–Independent Gene Expression," *Molecular and Cellular Biology*, 8(10):4395–4405, Oct. 1988.

Callis et al., "Introns Incease Gene Expression in Cultured Maize Cells," *Genes & Development*, 1:1183–1200, 1987.

Clancy et al., "Maize Shrunken–1 Intron and Exon Regions Increase Gene Expression in Maize Protoplasts," *Plant Science*, 98:151–161, 1994.

Curie et al., "Cis and Trans–acting Elements Involved in the Activation of *Arabidopsis Thaliana* A1 Gene encoding the Translation Elongation Factor EF–1α," *Nucleic Acids Research*, 19(6):1305–1310, 1991.

Curie et al., "Modular Organization and Developmental Activity of an *Arabidopsis Thaliana* EF–1α Gene Promoter," *Mol Gene Genet*, 238:428–436, 1993.

De Almeida et al., "Transgenic Expression of Two Marker Genes Under the Control of an Arabidopsis rbcS Promoter Sequences Encoding the Rubisco Transit Peptide Increase Expression Levels," *Mol Gen Genet*, 218:78–86, 1989.

Dean et al., "Sequences Downstream of Translation Start Regulate Quantitative Expression of Two Petunia rbcS Genes," *The Plant Cell*, 1:201–208, Feb. 1989.

Douglas et al., "Exonic Sequences are Required for Elicitor and Light Activation of a Plant Defense Gene, But Promoter Sequences are Sufficient for Tissue Specific Expression," *The EMBO Journal*, 10(7):1767–1775, 1991.

Fu et al., "High–Level Tuber Expression and Sucrose Inducibility of a Potato *Sus4* Sucrose synthase Gene Require 5' and 3' Flanking Sequences and the Leader Intron, " *The Plant Cell*, 7:1387–1394, Sep. 1995.

Gidekel et al., "The First Intron of the *Arabidopsis Thaliana* Gene Encoding for Elongation Factor 1β Contains an Enhancer–Like Element," *Gene*, 170:201–206, 1996.

Huang and Gorman, "Intervening Sequences Increase Efficiency of RNA 3' Processing and Accumulation of Cytoplasmic RNA," *Nucleic Acids Research*, 18(4):937–947, 1990.

Jefferson et al., "GUS Fusions: β–Glueuronidase as a Sensitive and Versatile Gene Fusion marker in Higher Plants," *The EMBO Journal*, 6(13):3901–3907, 1987.

Kavanagh et al., "Targeting a Foreign Protein to Chloroplasts Using Fusions to the Transit Peptide of a Chlorophyll a/b Protein," *Mol Gen Genet*, 215:38–45, 1988.

Klösgen and Weil, "Subcellular Location and Expression Level of a Chimeric Protein Consisting of the Maize *Waxy Transit* Peptide and the β–Glucuronidase of *Escherichai Coli* in Transgenic Potato Plants," *Mol Gen Genet*, 225:297–304, 1991.

Klösgen et al., "The Amyloplast–Targeting Transit Peptide of the Waxy Protein of Maize Also Mediates Protein Transport in Vitro Into Chloroplasts," *Mol Gen Genet*, 217:155–161, 1989.

Luehrsen and Walbot, "Addition of A–and U–Rich Sequence Increases the Splicing Efficiency of a Deleted Form of a Maize Intron," *Plant Molecular Biology*, 24:449–463, 1994.

Luehren and Walbot, "Intron Enhancement of Gene Expression and the Splicing Efficiency of Introns in Maize Cells," *Mol Gen Genet*, 225:81–93, 1991.

Maas et al., "The Combination of a Novel Stimullatory Element in the First Exon of the Maize *Shrunken–1* Gene with the Following Intron 1 Enhances Reporter Gene Expression up to 1000–Fold," *Plant Molecular Biology*, 16:199–207, 1991.

Mascarenhas et al., "Intron–Mediated Enhancement of Heterologous Gene Expression in Maize," *Plant Molecular Biology*, 15:913–920, 1990.

Norris et al., "The Intron of *Arabidopsis Thaliana* Polyubiquitin Genes is Conserved in Location and is a Quantitative Determinant of Chimeric Gene Expression," *Plant Molecular Biology*, 21:895–906, 1993.

Rose et al., "A Phosphoribosylanthranilate Transferase Gene is Defective in Blue Flurorescent *Arabidopsis Thaliana* Tryptonphan Mutants," *Plant Physiol*, 100:582–592, 1992.

Russell et al., "Plastid Targeting of *E. Coli* β–Glucuronidase and ADP–Glucose Pyrophosphorlase in Maize (Zea Mays L.) Cells," *Plant Cell Reports*, 13:24–27, 1993.

Vain et al., "Intron–Mediated Enhancement of Gene Expression in Maize (Zea Mays L.) and Bluegrass (Poa Pratensis L.)," *Plant Cell Reports*, 15:489–494, 1996.

Vasil et al., "Increased Gene Expression by the First Intron of Maize *Shrunken–1* Locus in Grass Species," *Plant Physiol*, 91:1575–1579, 1989.

Zhang et al., "arpkl, a Novel Ribosomal Protein Kinase Gene from *Arabidopsis*," *J Biological Chemistry*, 269(26):17586–17592, 1994.

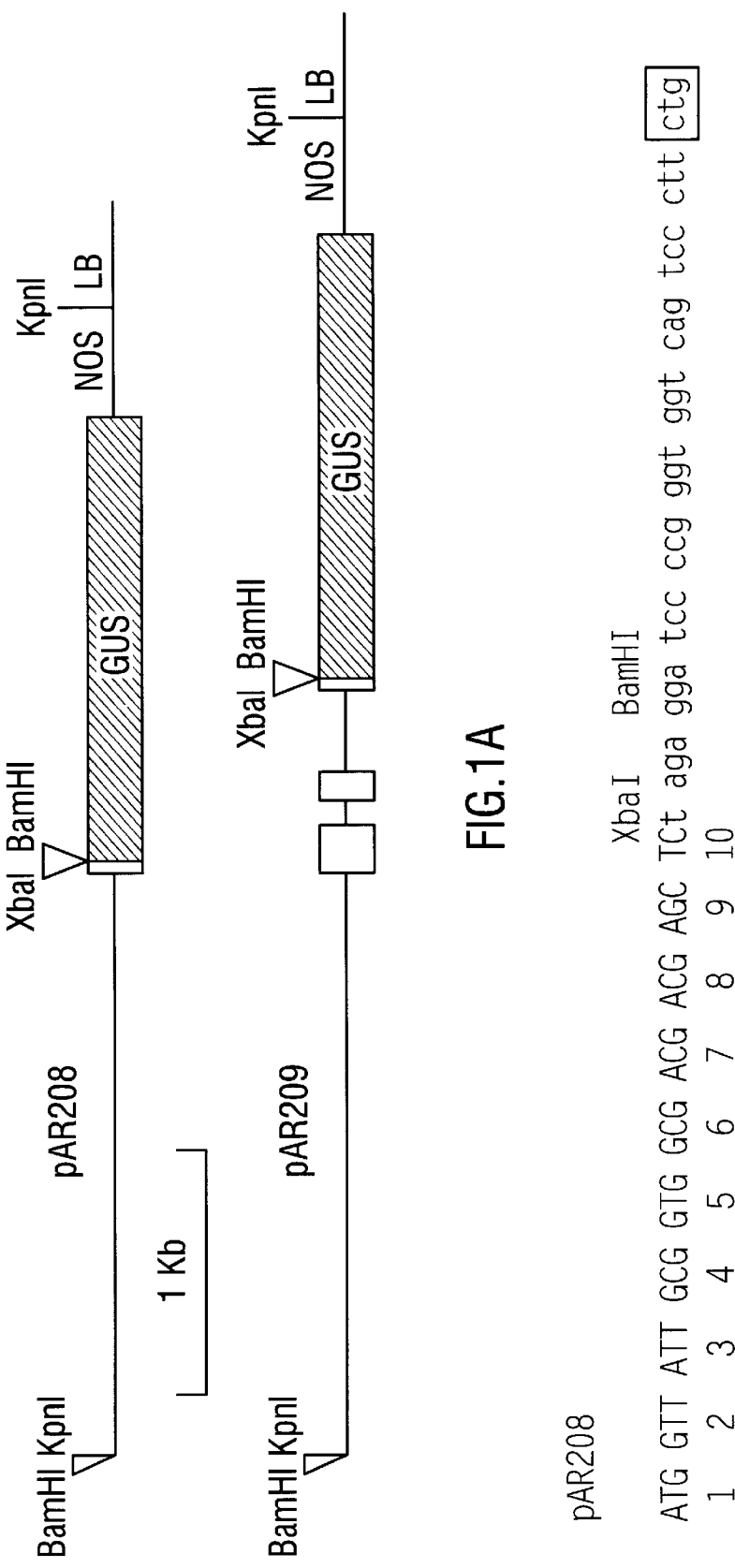

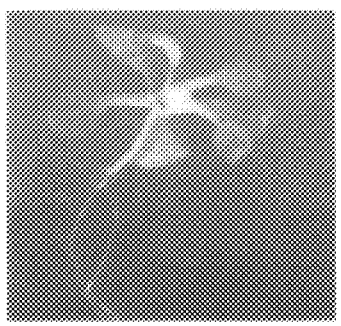 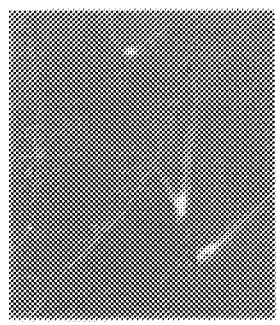  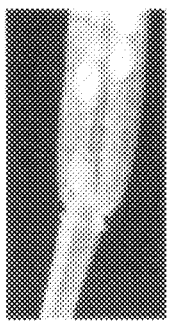
FIG. 2A  FIG. 2B  FIG. 2C  FIG. 2D
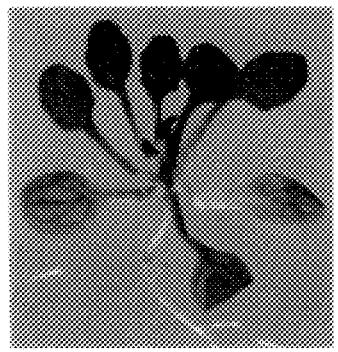 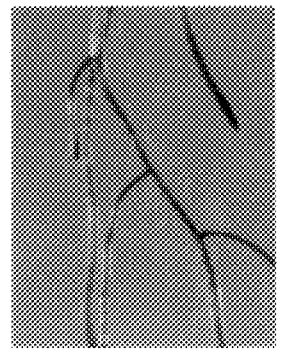  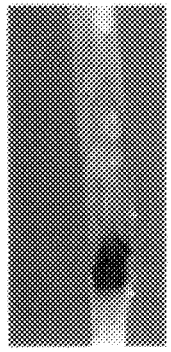
FIG. 2E  FIG. 2F  FIG. 2G  FIG. 2H

```
                    10        20        30        40        50        60
                    *         *         *         *         *         *
CT
TCGCAG|GTAAAGCCTCGATTTTTTGGGTTTAGGTGTCTGCTTATTAGAGTAAAAACACATCCTTTGA
 PstI 70        80        90       100       110
         *         *         *         *         *
AATTGTTTGTGGTCATTGATTGTGCTCTTGATCCATTGAATTGCTGCAG|CTCTT
                                              PstI
```

FIG. 9

METHODS AND COMPOSITIONS FOR ENHANCING THE EXPRESSION OF GENES IN PLANTS

The government owns rights in the present invention pursuant to grant number GM43134 from the National Institutes of Health and Presidential Young Investigator Award No. DMB-9058134 from the National Science Foundation.

BACKGROUND OF THE INVENTION

I. Field of the Invention

The present invention relates to the expression of exogenous proteins in plants. In particular, this invention relates to the use of downstream elements, specifically introns, to enhance expression of certain desired exogenous proteins in plants. Additionally, this invention relates to the use of methods to enhance expression of proteins of pharmacological interest in food plants. Methods and compositions for the enhancement of protein expression in plants and plant cells are disclosed.

II. Description of Related Art

The amount of protein that is synthesized from a gene is a function of several complex and interacting processes. Transcription, RNA maturation, and translation are each comprised of a large number of events, all of which are potentially regulated either independently or in concert. It is widely recognized that the upstream elements that control transcription and translation have very significant roles in determining the quantity, timing, and tissue specificity of gene expression. However, the sequences that are required for other aspects of expression (such as RNA processing) could be of equal or greater importance, and might be located in virtually any part of a gene.

While an enormous amount of research has demonstrated the importance of 5'elements in controlling gene expression, evidence shows that sequences downstream of the start of transcription can also have a major influence on the level or pattern of expression of plant genes. These elements include protein coding sequences (De Almeida et al., 1989; Douglas et al., 1991), introns (Callis et al., 1987; Clancy et al., 1994), and 5' or 3' transcribed but untranslated sequences (Dean et al., 1989; Larkin et al., 1993; Ulsamov and Folk, 1995). Despite the documented importance of downstream elements on gene expression, these regions are included in only a minority of reporter gene fusions designed to investigate the expression pattern of a gene.

The use of intronic portions of genes to aid in gene expression has also been reported for certain genes. For example, Callis et al. reported that at least the first intron of the maize (Zea mays L.) alcohol dehydrogenase -1 (Adh1) gene was probably required for significant levels of expression. (Callis et al., 1987). Further, Callis et al. reported that the position of the first intron with respect to the chimeric chloramphenicol acetyl transferase (cat) gene to be expressed was important to the level of expression observed. Illustrative of this point are the $pACI_1I_{8,9}A$ and $pAI_1CI_{8,9}A$ constructs wherein A represents Adh1, $I_X$ represents intron number x and C represents the cat gene. The construct wherein intron 1 was located upstream from the CAT gene showed a 110-fold increase in transient gene expression relative to $pACI_{8,9}A$, but a 21-fold increase relative to $pACI_1I_{8,9}A$ (i.e., 110-fold relative to a construct lacking the first intron, but 21-fold relative to one in which the first intron is downstream of the cat gene).

It has also been shown that compositions comprising the Zea mays L. (maize) Sh1 first intron fused to short sections of the flanking exons increases transient reporter gene expression in protoplasts of several grass species (Vasil et al., 1989). Further, Clancy et al. (1994) showed that in some instance, variations can be made in the intron structure and length without affecting the rate of enhancement of protein expression. Nevertheless, it is also known that not all genes containing introns require the presence of introns for efficient expression. For example, Chee et al., (1986) showed that removal of introns from bean phaseolin genes transferred to tobacco did not affect the expression of phaseolin protein in callus tissue.

The histochemical staining patterns previously reported for intronless GUS fusions to the tryptophan pathway genes TSB1, TSB2, ASA1, and ASA2 are similar to the patterns seen in lines containing an intronless GUS fusion to the tryptophan pathway gene PAT1 (Niyogi, 1993; Pruitt and Last, 1993). In light of the poor expression of PAT1-GUS in the absence of an intron detailed below, it seems plausible that these fusions might under-represent the expression of the genes under study. Consistent with this hypothesis, results analogous to those reported for PAT1-GUS fusions with and without introns were obtained for all three of the Arabidopsis genes encoding the next tryptophan pathway enzyme, phosphoribosylanthranilate isomerase (J. Li and R. L. Last, unpublished data). In each case, GUS fusions containing introns and the transit peptide give much more intense and widespread histochemical staining in transgenic plants than fusions lacking introns and the transit peptide.

A. Intron Enhancement

A positive effect of introns on gene expression has been observed for many plant genes. Expression of reporter genes under the control of the maize Adh1, Sh1, Bz1 or Act promoter is increased up to several hundred-fold by the inclusion of an intron (Callis et al., 1987; Oard et al., 1989; Vasil et al., 1989; Maas et al., 1991). Arabidopsis genes encoding polyubiquitin (Norris et al., 1993), transcription factor EF-1α, (Curie et al., 1991; Curie et al., 1993), and a protein kinase (Zhang et al., 1994) all have an intron in the 5' untranslated region. Fusion constructs containing any one of these introns are expressed at 2.5- to 1,000-fold higher levels than constructs lacking them. In all of these cases, the presence of an intron within a transcript leads to greater mRNA accumulation.

Despite the many examples of introns that increase gene expression, the mechanism of this enhancement remains unclear. One possibility is that an intron might contain an enhancer element that increases transcription. This is contradicted in the case of PAT1 by the nuclear run-on experiment showing only a minor difference in the rate of transcription of the transgene in lines containing PAT1-GUS fusions with or without introns. Alternatively, RNA splicing may influence RNA stability in some way. The lack of an additive effect as intron number is increased is more consistent with the latter hypothesis.

Several introns have been shown to increase mRNA accumulation by a mechanism related to intron splicing per se. In these cases the introns must be included within the transcribed portion of a gene and in the proper orientation in order to increase expression (Camis et al., 1987; Vasil et al., 1989). There is also a strong correlation between the ability of the first intron of the maize Adh1 gene to be spliced and its capacity to enhance gene expression, and mutagenesis studies indicate that the sequences required for splicing and gene enhancement localize to the same parts of the intron (Luehrsen and Walbot, 1991; Luehrsen and Walbot, 1994).

The sequences within an intron can be significantly modified by deletions or substitutions without interfering with the enhancement effect, as long as the intron retains the ability to be efficiently spliced. These observations suggest that the process of intron splicing is mechanistically coupled to the production of stable mRNA.

One potential explanation for such a connection is that introns could provide a necessary means for the association of pre-mRNA with a complex that includes splicing factors as well as those involved in other aspects of RNA maturation that contribute to mRNA stability. Capping, polyadenylation, and export from the nucleus to the cytoplasm all increase mRNA stability, and examples from several species suggest an interconnection between these processes and splicing. If splicing is not possible because a gene lacks its normal introns, several or all other mRNA maturation reactions could also be inhibited.

However, not all introns are able to increase the expression of a gene. Some plant genes are expressed equally well whether or not any introns are present (Chee et al., 1986; Kuhlemeier et al., 1988; Baker et al., 1994; Sistrunk et al., 1994), and many genes do not contain introns. Apparently the normal expression of some eukaryotic genes is intron-dependent while that of other genes is intron-independent.

The use of intronic sequences in the expression of exogenous proteins is not widespread. One probable reason is the difficulty of cloning an intron from one gene into another without also introducing non-intronic sequences that add undesired amino acids to the encoded protein, or create significant changes in the 5' non-coding regions that could alter gene expression. Furthermore, the intron-enhancement of gene expression has not been sufficiently characterized to predict which genes will benefit from the presence of an intron, or which introns will provide the maximum increase in expression of a particular gene in the desired species. In the small number of published reports where the benefits of including an intron were tested, the addition of an exogenous intron usually increased gene expression (for example Gallie and Young, 1994).

B. Tryptophan Pathway

The *Arabidopsis thaliana* tryptophan biosynthetic pathway provides a useful model for understanding the regulation of expression of a key plant metabolic pathway. The regulation of tryptophan biosynthesis is of particular interest because of the varied roles of the final product and other pathway derivatives. For example, as an amino acid tryptophan is presumably required by all cells that are translationally active, and the regulation of the pathway should reflect this need. However, the tryptophan pathway is also the source of numerous secondary metabolites including the growth regulator auxin (IAA), and inducible defensive compounds such as indolic glucosinolates and phytoalexins.

Given its diverse roles in plant growth and development, it is plausible that the pathway would be active in all cell types and developmental stages. However, the use of fusions of four different tryptophan pathway genes to the bacterial β-glucuronidase (GUS) reporter gene (Jefferson et al., 1987) have produced surprising, and in one case contradictory, results. Translational fusions of the promoter regions of TSB1 and TSB2, which encode the beta subunit of tryptophan synthase (Pruitt and Last, 1993), and ASA1 and ASA2, which encode the alpha subunit of anthranilate synthase (Niyogi, 1993), have been made. These were found to direct limited histochemical staining that is localized predominantly in the vasculature and apical and root meristems, an unexpected expression pattern for plastid-targeted proteins (Zhao and Last, 1995). Further analysis of the TSB1-GUS transgenic plants revealed discrepancies between the TSB1-GUS expression pattern and the distribution of TSB1 mRNA in several tissues, suggesting that the TSB1-GUS fusion might not accurately reflect the true pattern of TSB1 gene expression (Pruitt and Last, 1993). One potential reason for such an anomaly is that all of the sequences needed for gene expression may not be included in the fusion construct. In fact, each of the above mentioned gene fusions contained large regions (at least 1.5 kb) of sequences upstream of the transcription start site, but none contained more than 19 bp downstream of the start of translation.

Despite numerous examples that reveal the importance of transcribed sequences in gene expression, the vast majority of published reporter gene fusions include only sequences upstream of the translation start site in the fusion constructs. Although reporter gene fusions are very widely used in plant research to monitor gene expression, caution must be used to avoid potentially artifactual results (M ascarenhas and Hamilton, 1992; Vaucheret et al., 1992; Uknes et al., 1993). Failure to include all sequences required for proper expression can lead to misleading results. Poor translation of GUS reporter gene constructs is also a concern. The GUS gene used in transcriptional fusions is often derived from the closely related and commercially available plasmids pBI101, pBI121, and pBI221. Typically, the bacterial GUS gene is poorly translated in plants, but context improvements around the start codon of GUS were shown to lead to an eleven-fold improvement of translational efficiency in tobacco protoplasts (Kato et al., 1991). The GUS activity obtained from transcriptional fusions constructed using the GUS gene from any of the pBI vectors may therefore under-represent the strength of the promoter being studied.

SUMMARY OF THE INVENTION

The present invention seeks to overcome these and other drawbacks inherent in the prior art by providing a method and compositions that efficiently increase the expression of exogenous protein genes in plants and plant cells.

The present invention, in a general and overall sense, concerns a method of increasing exogenous protein expression in a cell. Generally, the method comprises the steps of making a DNA fusion construct comprising a promoter, intron 1 or intron 2 of the PAT1 gene, and a DNA segment encoding the exogenous protein one desires to express in the cell, and introducing the fusion into the host cell so that the cell expresses the fusion. In one preferred embodiment, the host cell is a plant cell.

Another aspect of the invention involves a method of increasing exogenous protein expression in a transgenic plant. Typically, this method comprises the steps of making a DNA fusion construct comprising a promoter, intron 1 or intron 2 of the PAT1 gene, and a DNA segment encoding the exogenous protein one desires to express in the transgenic plant, and expressing the fusion in a plant. In preferred embodiments, the DNA construct is introduced into the plant by *Agrobacterium tumefaciens*-mediated transformation (by either the vacuum infiltration or root explant method), particle bombardment, electroporation, or polyethylene glycol transformation. More preferably, the DNA construct is introduced into the plant using the vacuum infiltration method of *Agrobacterium tumefaciens*-mediated transformation. Additionally, the levels of exogenous protein expression are measured by enzyme assay, immunoblotting (Western blot), staining of SDS-PAGE protein gels, or enzyme-linked immunosorbent assay (ELISA). An example of a preferred method of measurement would be immunoblotting.

In one example the DNA construct of the invention comprises intron 1 of the PAT1 gene (SEQ ID NO:3). It has also been discovered that a construct comprising intron 2 of the PAT1 gene (SEQ ID NO:7) enhances transgene expression. Additionally, the DNA construct of the invention may comprise both intron 1 and intron 2 of the PAT1 gene (SEQ ID NO:3 and SEQ ID NO:7, respectively).

As used herein, the term "transgene" refers to a DNA fusion construct which has been introduced into a plant by transformation. The DNA fusion construct will typically comprise a promoter, PAT1 sequences, exogenous gene, marker gene and vector sequences, although it is contemplated that the construct may comprise less than all of the elements listed above.

The transgene will typically comprise a DNA segment encoding an exogenous protein fused to exons 1 and 2, 8 codons of exon 3, and intron 1 or intron 2 of the PAT1 gene. However, the transgene could also be a DNA segment encoding an exogenous protein fused to exons 1 and 2, 8 codons of exon 3 and intron 1 of the PAT1 gene (SEQ ID NO:12), or alternatively, a DNA segment encoding an exogenous protein fused to exons 1 and 2, 8 codons of exon 3 and intron 2 of the PAT1 gene (SEQ ID NO:13). Another example would be a DNA segment encoding an exogenous protein fused to exons 1 and 2, 8 codons of exon 3 and introns 1 and 2 of the PAT1 gene (SEQ ID NO:14). To facilitate the construction of such fusions, the DNA sequence recognized by the restriction endonuclease XbaI (TCTAGA) was introduced after the eighth codon of exon 3 (see SEQ ID NO:11) using the oligonucleotide OAR3 (SEQ ID NO:17).

Additional examples of the transgene comprise at least one intron of the PAT1 gene and a DNA segment encoding the entire chloroplast transit peptide or a DNA segment encoding a partial chloroplast transit peptide of the PAT1 gene. The chloroplast transit peptide is defined as comprising exon 1 and at least 10 codons of exon 2 of the PAT1 gene. The DNA segment encoding a partial chloroplast transit peptide will comprise at least 60 codons of the chloroplast transit peptide of the PAT1 gene. In a specific embodiment, the DNA segment of the fall chloroplast transit peptide is defined as SEQ ID NO:1 and that of the partial chloroplast transit peptide is defined as SEQ ID NO:2. Further, the invention comprises a slightly modified version of PAT1 intron 1 (SEQ ID NO:4, SEQ ID NO:5 and SEQ ID NO:6) created to enable its insertion into any PstI site.

Additional examples of the transgene of the invention are any genes, endogenous, exogenous, or any recombinant genes, that contain a natural or introduced PstI site into which any of these modified versions of PAT1 intron 1 has been inserted.

The DNA segment encoding an exogenous protein contemplated for use with the invention may encode a reporter gene. Possible reporter genes for use in conjunction with the present invention are listed in Table 1. In a preferred embodiment, the reporter gene is a β-glucuronidase (GUS) reporter gene, a chloramphenicol acetyl transferase (cat) gene or a luciferase (luc) gene. In a most preferred embodiment, the reporter gene is a GUS reporter gene. When a GUS reporter gene is used, it may be derived from pBI101, pBI101.2, pBI101.3, pBI121, pBI221, pGUSN358-S, or pCTGus.

TABLE 1

REPORTER GENES

| GUS | β-glucuronidase |
|---|---|
| gfp | Green Fluorescent Protein |
| cat | Choramphenicol Acetyl Transferase |
| lacZ | β-galactosidase |
| luc | Luciferase |

The invention also generally involves an isolated polynucleotide of the PAT1 gene comprising exon 1, 2 or 3 and intron 1 or intron 2. Preferably, the polynucleotide comprises exon 3 and intron 2 of the PAT1 gene (SEQ ID NO:20). However, the polynucleotide may also comprise exon 1 and intron 1 of the PAT1 gene (SEQ ID NO:21).

The DNA segment encoding an exogenous protein may alternatively encode a protein of pharmacological interest. Possible proteins of pharmacological interest generally include animal vaccine genes, human vaccine genes, antibodies which have been synthesized in plants, and enzymes of biosynthetic pathways that lead to the production of medicines. Preferred animal and human vaccine genes for use in conjunction with the present invention include those listed in Table 2. In a particular preferred embodiment, the DNA segment encodes the Hepatitis B surface antigen (HBsAg).

TABLE 2

VACCINE GENES

| HBsAg | Hepatitis B surface antigen |
|---|---|
| LTB | E. coli heat-labile enterotoxin B subunit |
| NVCP | Norwalk virus capsid protein |
| GAG | HIV gag protein |
| GST | Schistosoma 28 Kd glutathione-S-transferase |

The method of the invention generally involves expressing a desired exogenous protein in a plant. The plant in which exogenous protein expression is enhanced may be a tobacco plant, a potato plant, a tomato plant, a banana plant, an Arabidopsis plant or any member of the plant genus Brassica. In particular, the plant could be a potato plant.

The invention, in another sense, involves constructing a recombinant vector comprising a DNA segment encoding an exogenous protein gene operatively linked to a gene segment comprising intron 1 or intron 2 of the PAT1 gene. For example, the vector could comprise intron 1 of the PAT1 gene, or alternatively the vector could comprise intron 2 of the PAT1 gene. However, the vector could also comprise intron 1 and intron 2 of the PAT1 gene.

The vector described above may additionally comprise a DNA segment encoding a reporter gene. The reporter gene can be any one of those listed in Table 1, preferably the reporter gene could be the β-glucuronidase (GUS) gene. It is contemplated that, when the GUS reporter gene is used, it may be derived from a number of sources, such as pBI101, pBI101.2, pBI101.3, pBI121, pBI221, pGUSN358-S, or pCTGus.

Another aspect of the invention involves constructing an expression vector comprising any of the DNA constructs or polynucleotides described above. The expression vector will typically transfect a cell, preferably a plant cell. In particular, the expression vector may transfect a wild-type Arabidopsis cell. The plant cell is typically transformed with any one of the transgenes described above and comprises an increased number of RNAs encoding an exogenous protein in comparison to a plant cell not transformed with the transgene.

The invention may also be defined generally as a recombinant host cell comprising an exogenous fusion protein. The exogenous fusion protein may comprise any one of the above described transgenes, which include an operative link to a DNA segment encoding an exogenous protein one desires to express. In one embodiment, the exogenous protein is introduced into the recombinant cell by means of a recombinant vector. Alternatively, the recombinant host cell may comprise any one of the transgenes described above which could also be introduced into the recombinant cell by means of a recombinant vector.

A specific illustration of the method of the invention would involve constructing gene fusions comprising any part of the PAT1 gene and a DNA segment encoding an exogenous protein one desires to express, and introducing the fusion into wild-type Arabidopsis. The transgene may be any one of the transgenes described above and may be introduced into the plant by Agrobacterium tumefaciens-mediated transformation (by either the vacuum infiltration or root explant method), particle bombardment, electroporation, or polyethylene glycol transformation. Preferably, the fusion of transgene and exogenous gene will be introduced into the Arabidopsis by means of the vacuum infiltration method.

The transformed plant line of the invention may comprise a DNA segment encoding the entire chloroplast transit peptide of the PAT1 gene and intron 1 or intron 2 of the PAT1 gene. For example, the transformed plant line may comprise a DNA segment encoding the entire chloroplast transit peptide of the PAT1 gene and intron 1 of the PAT1 gene (SEQ ID NO:15). The chloroplast transit peptide may be defined as having the nucleotide sequence of SEQ ID NO:1.

The plant line described above is typically prepared by the process of creating a translational fusion protein gene and introducing the fusion into a plant. One example of a plant to be transformed by the methods of the invention is a wild-type Arabidopsis. However, the plant line may also be a food plant. For example, the plant could be a tobacco plant, a potato plant, a tomato plant, a banana plant or any member of the plant genus Brassica. Preferably, the plant will be a potato plant.

The fusion introduced into the transformed plant line will typically comprise an exogenous protein gene operatively linked to exons 1 and 2, 8 codons of exon 3 and intron 1 or intron 2 of the PAT1 gene. In one example, the fusion could comprise an exogenous protein gene operatively linked to exons 1 and 2, 8 codons of exon 3 and intron 1 of the PAT1 gene. However, the fusion could also comprise an exogenous protein gene operatively linked to exons 1 and 2, 8 codons of exon 3 and intron 2 of the PAT1 gene. Alternatively, the fusion could comprise an exogenous protein gene operatively linked to exons 1 and 2, 8 codons of exon 3 and intron 1 and intron 2 of the PAT1 gene. Typically, the fusion will be made using an XbaI site introduced after the 8th codon of exon 3. However, it will be understood by one of skill in the art other methods may be used to construct the fusions described herein.

Alternatively, the gene introduced into the transformed plant line will comprise an exogenous protein gene operatively linked to its own promoter or another promoter that is active in plants. This gene will contain the cloned PAT1 intron 1 that has been inserted using a natural or engineered PstI site for the purpose of increasing the expression of that exogenous protein gene.

The invention also generally involves a cultivated, transgenic food plant, the genome of which has been augmented through the genomic introduction of a preselected exogenous protein gene not found in the genome of non-transformed parentage of the plant where the plant is preparable by a process that includes the steps of: preparing a nucleic acid composition including the exogenous protein gene one desires to introduce into the genome of a food plant, where the exogenous protein gene is operatively linked to at least one intron of the PAT1 gene; contacting recipient food cells with the composition under conditions allowing the uptake of the exogenous protein gene by recipient cells; regenerating food plants from recipient cells which have received the exogenous protein gene; and identifying a fertile, transgenic food plant whose genome has been augmented relative to that of the corresponding non-transgenic recipient cells through the stable introduction of the exogenous protein gene. Preferred embodiments of the invention comprise the progeny of the above described plant, seed obtained from the above described plant, or cells obtained from the above described plant. The composition to be introduced into the plant may also comprise any one of the transgenes described above.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A and FIG. 1B. Structures of pAR208 and pAR209.

FIG. 1A Schematic representations of the fusion constructs. Thin lines represent PAT1 promoter regions and introns, open boxes are PAT1 protein coding exons, the filled box is the GUS gene, and thicker lines are other sequences as indicated. Abbreviations: GUS, uidA b-glucuronidase gene from E. Coli ; NOS, nopaline synthase terminator; LB, left border sequence of T-DNA.

FIG. 1B Details of the fusion junction sequences. PAT1 sequences are shown in upper case with the codons numbered, vector sequences are in lower case, and the GUS start codon which was previously modified to CTG (Pruitt and Last, 1993). is enclosed in a box. The sequence of pAR208 is shown from the start of translation, and the vertical line in the pAR209 sequence shows the boundary between intron 2 and exon 3 of PAT1.

FIG. 2A, FIG. 2B, FIG. 2C, FIG. 2D, FIG. 2E, FIG. 2F, FIG. 2G and FIG. 2H.

Histochemical staining of plants transformed with pAR208 or pAR209.

FIG. 2A Leaves of pAR208 transgenic line 1–4.

FIG. 2B Roots of pAR208 transgenic line 1–1.

FIG. 2C Flowers of pAR208 transgenic line 1–1.

FIG. 2D Immature seed pod of pAR208 transgenic line 1–1.

FIG. 2E Leaves of pAR209 transgenic line A4–1.

FIG. 2F Roots of pAR209 transgenic line 2–1.

FIG. 2G Flowers of pAR209 transgenic line 2–1.

FIG. 2H Immature seed pod of pAR209 transgenic line 2–1.

The leaves in FIG. 2A and FIG. 2E and the roots in FIG. 2B and FIG. 2F were from plants grown for 15 days on sterile agar medium, while the flowers in FIG. 2C and FIG. 2G, and the immature seed pods in FIG. 2D and FIG. 2H, were from plants grown on agar for three weeks, then in soil for an additional two weeks.

Figure 3A:
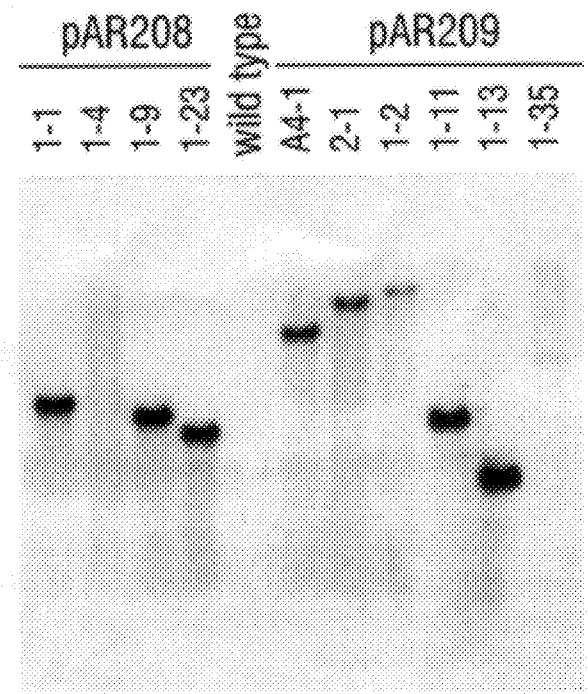
Figure 3B:
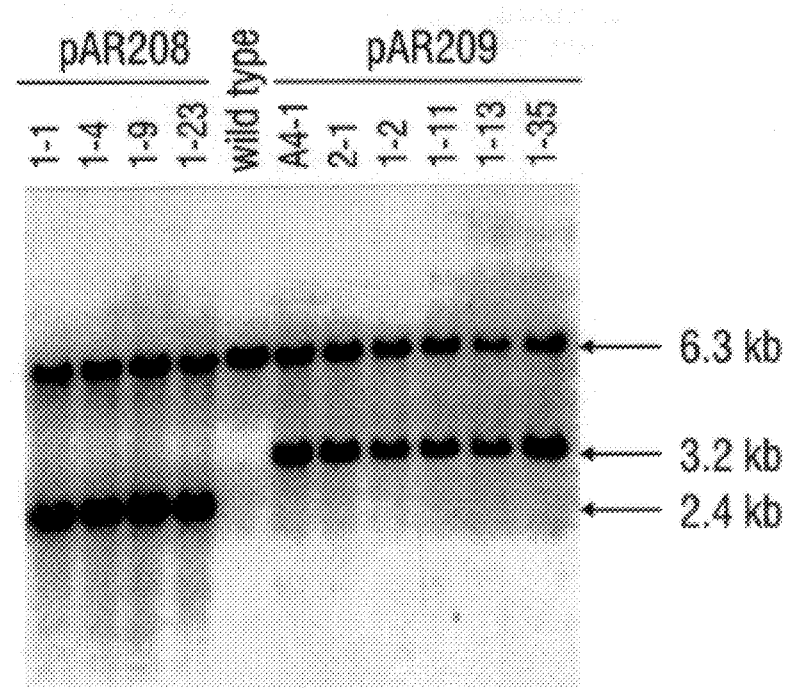

FIG. 3A and FIG. 3B. Analysis of Transgenic Lines by Genomic DNA Gel Blot Hybridization.

Blots of BamHI-digested genomic DNA from lines transformed with pAR208, wild-type plants, or pAR209 transgenic lines as indicated.

FIG. 3A Filter probed with the 2.2 kb GUS gene of pAR140.

FIG. 3B Filter probed with the 1.2 kb PAT1 promoter fragment of pAR170.

FIG. 3A shows four pAR208 lines and six pAR209 lines which were identified that contain single and unique sites of transgene insertion. The distinct size of the GUS-hybridizing BamHI fragment from each line shows that all are independent transformants. One discrete band is observed in most lanes, confirming that a single transgene is present in each line. The smear of hybridization in lanes from pAR208 line 1–4 and pAR209 line 1–35 could be explained if the GUS-containing BamHI fragment is very large, because it would be susceptible to shearing during DNA isolation and may also transfer poorly to the membrane. FIG. 3B show that each pAR208 and pAR209 line contains an additional PAT1 promoter fragment of the size expected for an unrearranged insertion of the transgene. Each pAR208 and pAR209 line contains a 2.4 kb or 3.2 kb BamHI fragment respectively, which corresponds to the size of the PAT1 promoter fragment in the pAR208 and pAR209 plasmids. The endogenous PAT1 gene is on a 6.3 kb BammE fragment, seen in all transgenic lines and wild-type plants. The similar band intensities of the endogenous and transgenic PAT1 fragments is further evidence that each line contains a single transgene.

Figure 4:
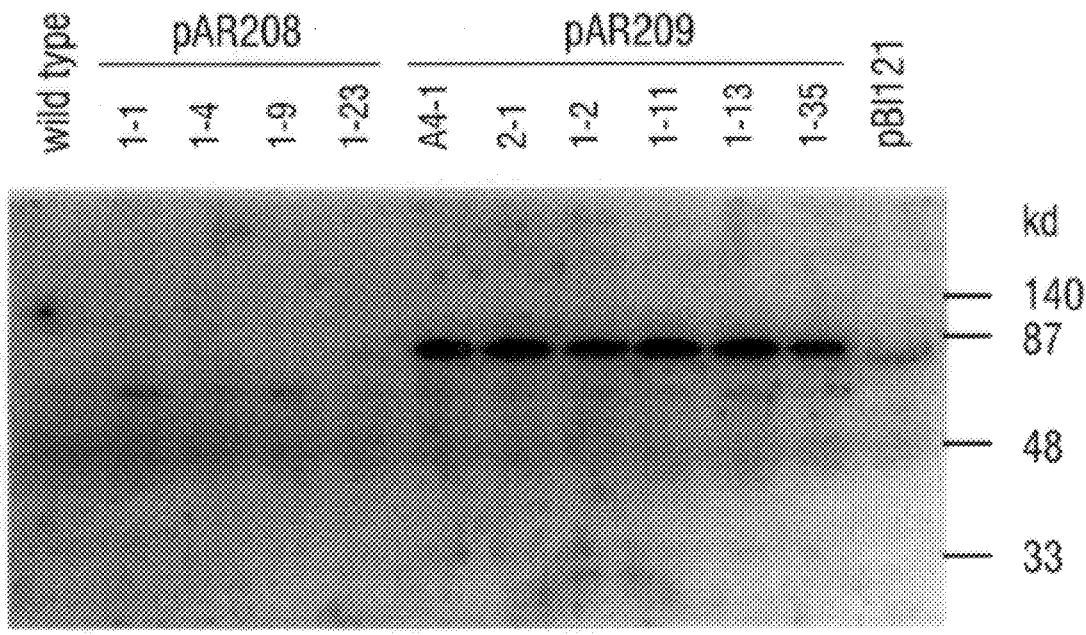

FIG. 4. Immunological Detection of GUS Protein in Transgenic Plants. Immunoblot analysis of protein extracts from wild type and pAR208, pAR209, and pBI121 transgenic plants, probed with anti-GUS antibodies. The position of migration of protein size markers is indicated. The data presented here can be used to estimate the approximate location of the PAT1 transit peptide cleavage site. The fusion protein encoded by pAR209 migrates in an SDS polyacrylamide gel as if it were approximately 5 kd larger than the GUS protein encoded by pBI121. However, this difference in migration is less than the 13 kd difference predicted if the entire transit peptide remained fused to GUS. This suggests that ~80 of the $NH_2$-terminal PAT1 residues are removed by chloroplast signal peptidase, leaving roughly 40 residues of PAT1 and 10 amino acids encoded by linker sequences fused to GUS in the mature fusion protein.

Figure 5A:
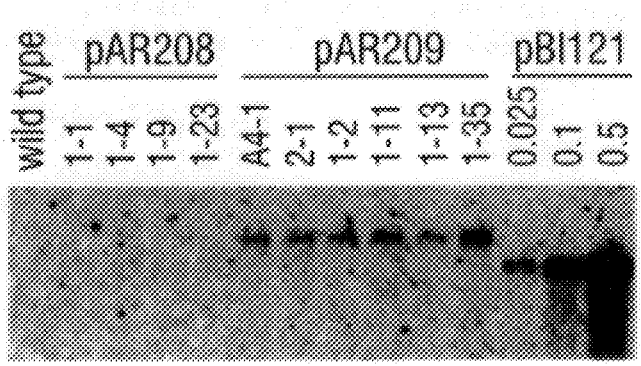
Figure 5B:

FIG. 5A and FIG. 5B. Analysis of GUS mRNA in Transgenic Plants.

FIG. 5A Gel blot of RNA from transgenic lines hybridized with the GUS probe from pAR140. Total RNA from wild type and pAR208 or pAR209 transgenic lines (5 μg per lane), or a pBI121 transgenic line (0.025 μg, 0.1 μg, or 0.5 μg), was loaded per lane as indicated. mRNA that hybridized to the GUS probe was readily detected in all of the pAR209 lines, but was not seen in RNA from pAR208 lines.

FIG. 5B Ethidium bromide-stained gel used for the blot shown in (A). The ethidium-stained gel confirms that equivalent amounts of RNA are present in each lane.

Figure 6:
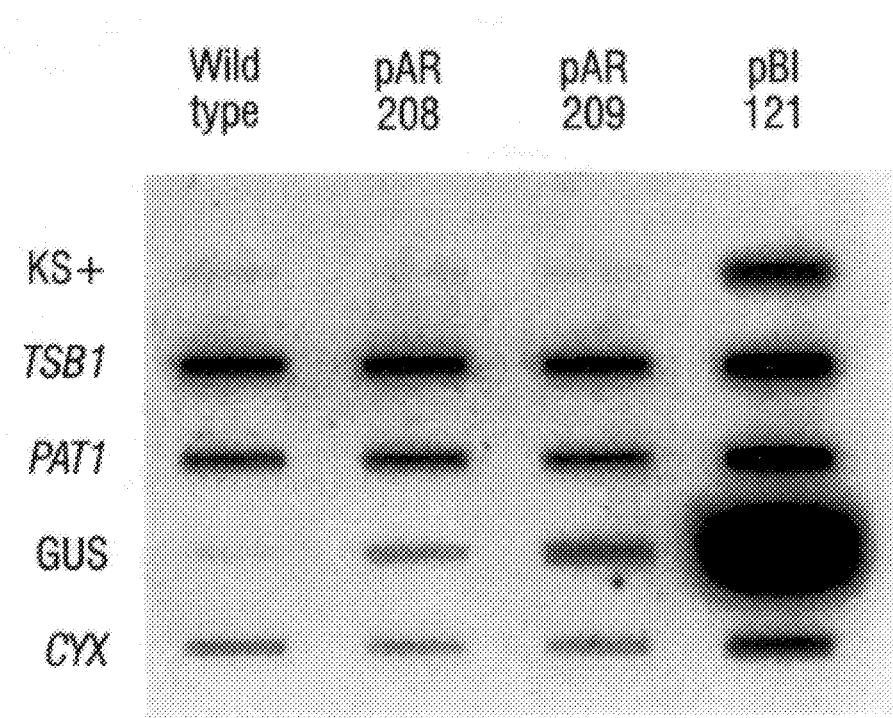

FIG. 6. Nuclear Run-on Analysis of Transgenic Plants. Nuclei isolated from the lines indicated along the top of the figure were incubated in the presence of $^{32}P$-UTP to allow run-on transcription. The radioactive RNA synthesized by the nuclei was hybridized to strips of nitrocellulose filters to which 10 mg of each of the cloned DNAs listed on the left had been affixed by slot-blotting. Nuclear run-on analysis was used to ascertain whether the transgenic lines differed in the rate of transcription. RNA synthesized by wild-type, pAR208 and pAR209 nuclei hybridize equally to the PAT1, TSB1, and CYX1 DNAs, confirming that equivalent amounts of labeled RNA were used in each hybridization. In addition to hybridizing very strongly to the GUS gene, RNA synthesized by nuclei from the pBI121 line hybridized to the vector DNA negative control. It also showed more hybridization to the PAT1, TSB1 and CYX clones than did the RNA from the other lines, even though an equal number of counts of radioactive RNA were used in each hybridization. These results are probably due to the 585 bp of M13 sequences including the lacI gene that lie immediately downstream of the nopaline synthase terminator at the 3' end of the GUS gene in pBI121. All of the plasmids used in FIG. 6 contain lacI, and the observed hybridization to the negative control and the additional hybridization to all of the other DNAs could be accounted for if 15% of the GUS transcripts extend beyond the nopaline synthase terminator into lacI sequences.

Figure 7:
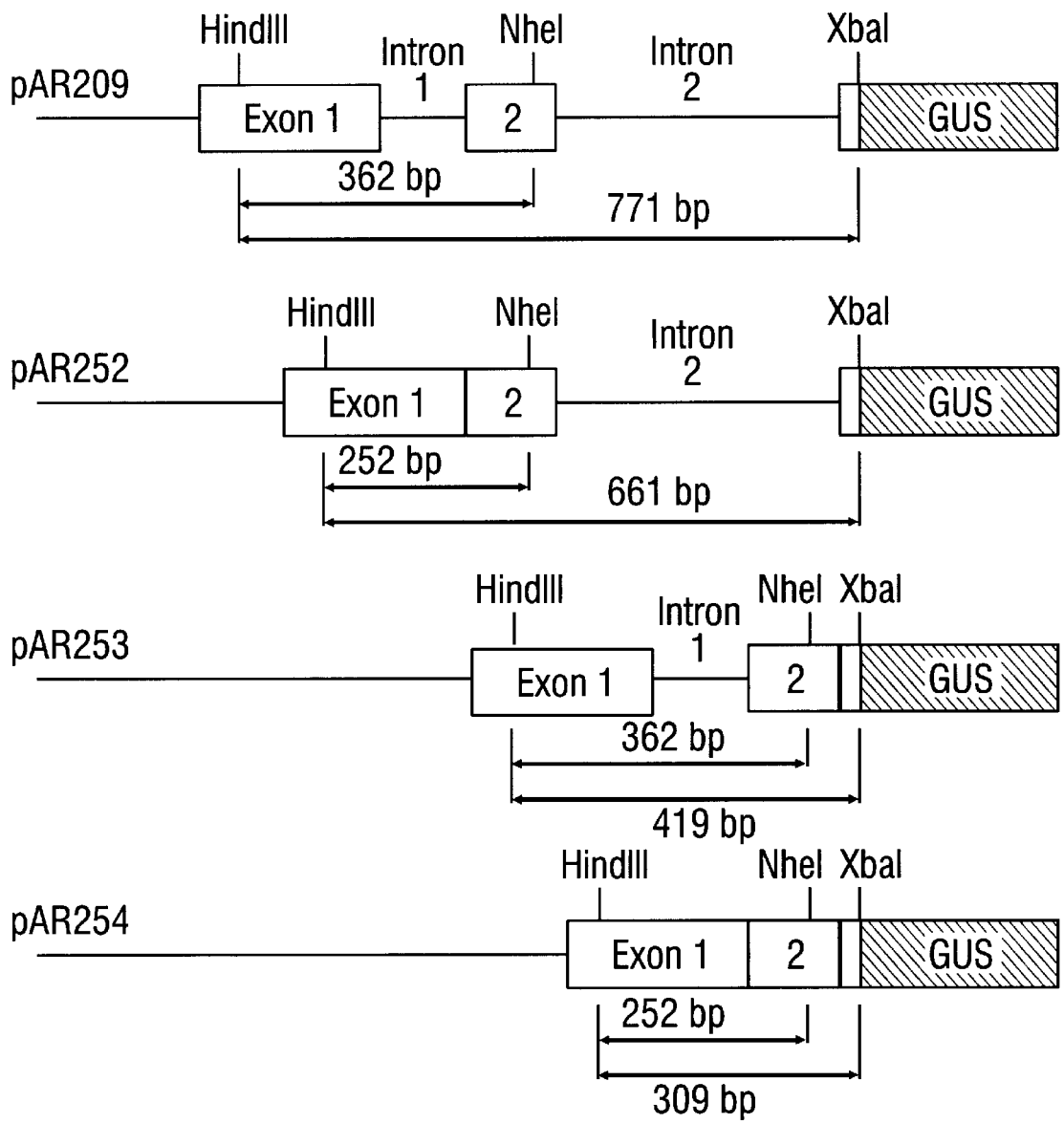

FIG. 7. Details of pAR252, pAR253, and pAR254 Structures. Thin lines represent PAT1 promoter regions and introns, open boxes are PAT1 protein coding exons, and the filled box is the GUS gene. In all other respects, the structure of pAR252, pAR253, and pAR254 are the same as for pAR209 (see FIG. 1).

FIG. 8A, FIG. 8B, FIG. 8C, FIG. 8D, FIG. 8E, and FIG. 8F. Histochemical Staining of Transgenic Lines Containing pAR252, pAR253, or pAR254. Plants were grown on sterile agar medium for 14 days before incubating in X-Gluc for three hours at 37° C.

Figure 8A:
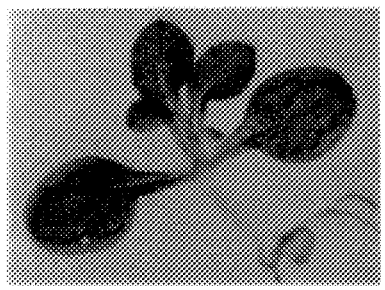

FIG. 8A Leaves of pAR252 transgenic line B2.

Figure 8B:
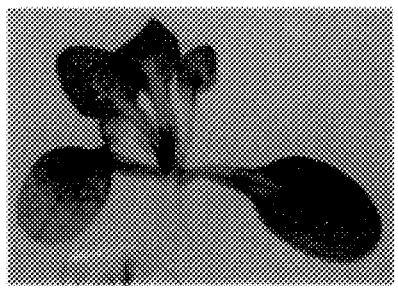

FIG. 8B Leaves of pAR253 transgenic line B4.

Figure 8C:
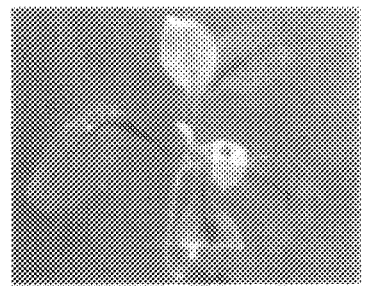

FIG. 8C Leaves of pAR254 transgenic line A1.

Figure 8D:

FIG. 8D Roots of pAR252 transgenic line A13.

Figure 8E:
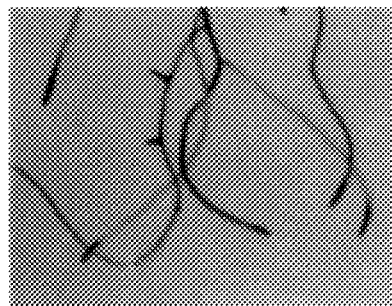

FIG. 8E Roots of pAR253 transgenic line A4.

Figure 8F:
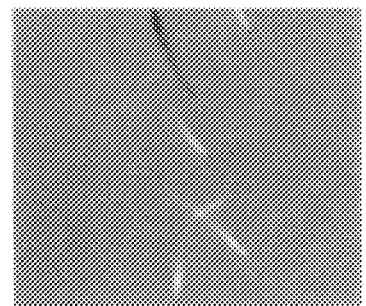

FIG. 8F Roots of pAR254 transgenic line B6.

FIG. 9. Nucleotide sequence of PAT1 intron 1. The vertical lines denote the intron boundaries, and matches to the branch point consensus sequence (PyTNAN) and PstI sites are underlined. The nucleotide changes to create a PstI site immediately 5' to the intron are indicated above the sequence.

DESCRIPTION OF ILLUSTRATIVE EMBODIMENTS

The present invention addresses one or more of the foregoing or other shortcomings in the prior art by providing compositions and methods for the enhanced expression of desired exogenous protein genes in transgenic plants. The invention further provides compositions and methods for the preparation of stably transformed cells exhibiting significant amounts of desired exogenous protein genes. Still further, the invention provides compositions and methods for the subsequent regeneration of fertile, transgenic plants and progeny containing the desired exogenous protein genes. The invention particularly provides techniques for the preparation of transgenic, fertile plants, into which have been introduced exogenous genes of pharmacological interest.

The invention thus relates generally, in certain embodiments, to methods for the production of transgenic plants. As used herein, the term "transgenic plants" is intended to refer to plants that have incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression. It is contemplated that in some instances the genome of transgenic plants of the present invention will have been augmented through the stable introduction of the transgene. However, in other instances, the introduced gene will replace an endogenous sequence.

Exemplary genes which may be introduced include, for example, DNA sequences or genes from another species, or even genes or sequences which originate with or are present in the same species, but are incorporated into recipient cells by genetic engineering methods rather than classical reproduction or breeding techniques. However, the term "exogenous", is also intended to refer to genes which are not normally present in the cell being transformed, or perhaps simply not present in the form, structure, etc., as found in the transforming DNA segment or gene, or genes which are normally present yet which one desires, e.g., to have over-expressed. Thus, the term "exogenous" gene or DNA refers to any gene or DNA segment that is introduced into a recipient cell, regardless of whether a similar gene may already be present in such a cell. Introduced, in this context, is known in the art to mean introduced by the hand of man.

Exemplary compositions for enhancing exogenous protein gene expression include transgenes comprising portions of the PAT1 gene of *Arabidopsis thaliana*. However, it is contemplated that many introns from many genes in many species will enhance expression. For example, introns from the maize Adh1, Sh1, and Bz1 genes and the rice ActI gene are expected increase the expression of several different genes in maize and other monocot species such as rice or wheat. Likewise, the introns from the Arabidopsis atpk1, EF-1α, UBQ3, and UBQ10 genes would likely increase expression of genes in Arabidopsis and other dicots such as tobacco, tomato and potato.

For purposes of the invention, the PAT1 gene may be derived from pAR 119, pAR125, pAR137, pAR138 or pAR139 (all described in Rose et al. 1992). The transgenes of the invention incorporate one or both of the first two introns of the PAT1 gene (SEQ ID NO:3 or SEQ ID NO:7, respectively). Alternatively, transgenes of the invention may incorporate a modified intron 1 of the PAT1 gene (SEQ ID NO:4, SEQ ID NO:5 or SEQ ID NO:6). For purposes of the invention, this modified intron 1 may be derived from pAR255, pAR256, pAR257, pAR258, PAT-pKS4 or PAT-pKS8.

Transgene as used herein refers to a gene that has been transferred into a species by some method of transformation. As such, the term "transgene" refers to compositions which include the contemplated portions of the PAT1 gene fused or operatively linked to a DNA segment encoding the exogenous protein one desires to express. Exemplary compositions may further include a promoter sequence or segment at the 5' end of the PAT1 gene. It is contemplated that sequences upstream of the first exon may constitute the PAT1 promoter normally required for PAT1 expression. For example, it is known that a segment of approximately 1.1 Kb upstream of the first exon is sufficient for expression. Further, the inventors' studies show that expression was achieved with a segment of approximately 2.4 Kb of 5' PAT1 sequences (Example 3). However, one of skill in the art would understand that other promoters may also be able to drive expression of PAT1 or PAT1 fusions.

As used herein, the term "operatively linked" means that a promoter is connected to a coding region in such a way that the transcription of that coding region is controlled and regulated by that promoter. Means for operatively linking a promoter to a coding region are well known in the art.

The slightly modified version of PAT1 intron 1 was created to enable its insertion into any PstI site. The 6 nucleotides at the 3' end of exon 1 are TCGCAG (FIG. 9). Using a mismatching PCR primer to amplify this intron, the order of the first two nucleotides was reversed to create a PstI site (CTGCAG) that immediately abuts intron 1. Because the last 6 nucleotides that naturally form the 3' end of intron 1 are also CTGCAG, the entire intron can be inserted into any PstI site, precisely introducing a complete natural intron with no other sequences and without altering reading frame. Other advantages of this intron cassette are that it is relatively small (110 bp) and can therefore be easily modified in vitro, it can act as a negative control when inserted in the wrong orientation, and its effect on gene expression is at least 5-fold.

I. Introns

Introns are regions of gene sequences which are spliced after transcription from the primary RNA transcript to generate the mature RNA. While largely embodied in eukaryotic genes such as genes encoding proteins, tRNAs, and rRNAs, few prokaryotes have intron-containing genes. In general, the number and organization of introns within genes varies greatly depending on the gene. For example, some genes, such as the chicken pro-$\alpha_2$ and the collagen gene, have as many as 50 introns or more. Additionally, the size of each intron within the gene may vary greatly. This difference is illustrated by a comparison of a gene of the SV40 virus, which contains an intron with 31 nucleotides, and the human dystrophin gene, which contains an intron with more than 210,000 nucleotides. Typically, though, simple eukaryotes have few intron-containing genes as compared with higher eukaryotes.

The intronic structure for nuclear-encoded (eukaryotic) proteins includes conserved 5' and 3' splice sites with a base sequence of 5' GU—AG3'. These regions are removed from the primary transcript by spliceosomes. Splicing occurs before the gene is transported over the nuclear membrane into the cytoplasm for translation and is a two-step process. In the first step, the intron is cleaved at the 5' end and the guanosine residue (G) covalently linked through a 2'–5' phosphodiester bond to an adenine residue (A) within a recognition element termed the branch point sequence (BPS). This adenine residue is typically located 20–50 nucleotides upstream from the 3' splice site. It is believed that the cleavage and branch formation occur simultaneously.

The second step of intron splicing involves cleavage at the 3' site and ligation of exons. After the intron is fully cleaved, it contains the 2'–5' linkage at the branch point and is released. The phosphate moieties produced during the cleavage process at the 5' and 3' splice sites remain in the products, one being attached to the released intron at the 5' end and the other being inserted at the ligation point in the resulting exon-containing gene. Besides the conserved sequences at the intron 5' and 3' sites, the BPS and flanking exon sequences also participate in the splicing process and splice site recognition.

While some introns require the aid of spliceosomes for splicing, others catalyse their own removal in the absence of any protein. These introns, termed "self-splicing" introns, splice with either a guanosine cofactor for autocatalytic splicing (group I introns) or with only the hydroxyl group of an adenine at the 3' end of the intron at the 5' splice site (group II introns).

It has been discovered that the first two introns of the PAT1 gene play a role in enhancing the expression of exogenous protein genes. The PAT1 gene encodes phosphoribosylanthranilate transferase (Rose et al., 1992), which catalyses the second committed step of tryptophan biosynthesis. This gene is known to be the site of mutations in the blue fluorescent trp1 mutants and appears to be a single copy gene (Rose et al., 1992). In particular, the present inventors have created constructs comprising the first two exons, either or both of the first two introns, and a portion of the third exon of the PAT1 gene for use in enhancing gene expression. Typical constructs of the invention have the structure $E_1I_1E_2I_2E_3$ (SEQ ID NO:14), $E_1I_1E_2E_3$ (SEQ ID NO:12), or $E_1E_2I_2E_3$ (SEQ ID NO:13) where $E_x$ represents exon number x and $I_y$ represents intron number y. It has also been discovered that either or both of the first two introns enhance the expression of transgenes comprising the first, second, and third exon of the PAT1 gene fused to the GUS reporter gene. The first intron of PAT1 has been modified to allow its insertion into a PstI site within any gene, precisely introducing a complete natural intron with no other sequences and without altering reading frame.

The introns of the present invention have the sequences specified in SEQ ID NO:3, SEQ ID NO:4, SEQ ID NO:5, SEQ ID NO:6 and SEQ ID NO:7, representing intron 1, three modified intron 1s, and intron 2 of the PAT1 gene, respectively. The exons included in the present invention have the sequences defined by SEQ ID NO:8, SEQ ID NO:9 and SEQ ID NO:10, respectively. The transgenes of the present invention have the sequences defined by SEQ ID NO:12–14.

The DNA constructs of the invention may be fused or operatively linked to a reporter gene to allow determination of levels of enhanced expression resulting from the PAT1 sequences. Possible reporter genes for use in conjunction with the present invention are listed in Table 1 (page 10). Preferably, the reporter gene is a β-glucuronidase (GUS) reporter gene, a chloramphenicol acetyl transferase (cat) gene or a luciferase (luc) gene. Most preferably the reporter gene is a GUS reporter gene.

It is contemplated by the inventors that fusions comprising the DNA constructs of the invention may also include DNA segments encoding proteins of pharmacological interest. Exemplary proteins contemplated for use in the present invention include, but are not limited to, those listed in Table 2 (page 11).

The expression and regulation of the PAT1 gene was investigated using several translational fusions to the GUS reporter gene. The GUS gene was fused either to the first protein coding exon near the start codon or to the third exon of PAT1 using introduced XbaI restriction enzyme sites. The inventors show that transgenic plants containing fusions to the third exon have high GUS enzyme activity throughout the plant if at least one of the first two PAT1 introns is included in the fusion. Plants transformed with constructs that lack introns, with GUS fused either to the first or third PAT1 exon, have significantly lower GUS activity that is restricted to a limited number of tissues. The fusions containing both introns give rise to higher GUS enzyme activity, fusion protein accumulation, and steady-state level of PAT1-GUS mRNA than fusions lacking introns and the transit peptide, but both constructs are transcribed at similar rates. These results demonstrate that introns influence PAT1 expression by increasing RNA accumulation, and illustrate some potential artifacts of the GUS fusion technique.

Additionally, two translational fusions of the PAT1 promoter to the GUS gene were created, as shown in FIG. 1, to test the influence of downstream sequences on expression, and to control for effects of the PAT1 transit peptide on fusion protein activity. These two constructs differ only in the amount of the PAT1 transcribed region included: pAR208 contains the first 10 codons of PAT1, while pAR209 includes all of exons 1 and 2, the first two introns, and 8 codons of exon 3. The 118 amino acids of PAT1 in pAR209 contain the entire chloroplast transit peptide, and presumably include a portion of the $NH_2$-terminus of the mature PAT1 protein.

Exon 1 and part of exon 2 make up the chloroplast transit peptide of the PAT1 gene. These exons contain nucleotides which code for amino acids necessary to guide the gene to be expressed into the chloroplast. Thus, it is contemplated that the DNA constructs of the present invention comprising the entire chloroplast transit peptide, including intron 1 would also enhance gene expression. Additionally, DNA constructs comprising a portion of the chloroplast transit peptide and intron 1 would enhance gene expression.

It is contemplated that variants of the introns of the present invention will also be useful. Variants of introns are defined as sequences which are equivalents of the intronic sequences of the present invention. For example, equivalent variants of the present invention may have a 90 percent similarity to the sequences of the introns of the present invention. Alternatively, variants may have an 80 percent similarity and still be equivalent within the parameters of the present invention. By way of illustration, three versions of the modified intron 1 that differ in sequence but are expected to be functionally equivalent are presented in SEQ ID NO:4–6. These were derived from the Col (SEQ ID NO:4) or Ler (SEQ ID NO:5) ecotypes of Arabidopsis, and they differ in length (110 bp vs. 128 bp) and nucleotide composition. The hybrid intron (SEQ ID NO:6) is mostly the Col sequence with a small amount of Ler sequence at the 5' end of intron 1.

Equivalents for purposes of the present invention include sequences which are equivalent both structurally and functionally. For example, it is contemplated that variants or equivalents of the introns of the present invention may be produced by creating a structural change in the sequence. For example, equivalents of the introns of the present invention may include several nucleotides more than the introns of the invention. Or, in the alternative, they may be several nucleotides shorter than the introns of the invention. For example, it has been found that the PAT1 gene from the Ler ecotype of Arabidopsis is quite different from the gene from the Col ecotype, however, both genes and their introns are expected to function in the same way.

The fusions in pAR208 and pAR209 were introduced into wild-type Arabidopsis by Agrobacterium tumefaciens-mediated transformation, and the pattern of GUS expression was determined by histochemical staining. As might be expected for fusions to the promoter of a gene that encodes a "housekeeping" enzyme, transgenic plants transformed with pAR209 (henceforth called pAR209 lines) show intense staining in virtually all parts of the plants. The strong GUS activity in tissues that lack chloroplasts (such as roots) indicates that expression of PATI is not limited to photosynthetically active cells, and suggests that the PAT1 transit peptide can direct the import of proteins into plasmids other than chloroplasts. In contrast to the widespread staining of pAR209 lines, plants transformed with pAR208 (pAR208 lines) show weak histochemical staining only in the root tips and at the base of the leaf petioles in a pattern similar to that seen from TSB1-GUS fusions (Pruitt and Last, 1993).

Two lines of evidence suggest that the difference in GUS activity observed in pAR208 and pAR209 lines may be quantitative rather than qualitative. First, those tissues that show any histochemical staining in pAR208 lines, such as root tips and the base of immature seed pods are the regions of most intense staining in pAR209 lines. Furthermore, the staining observed in pAR209 lines treated very briefly with chromogenic substrate resembles the pattern of pAR208 lines stained for a longer time.

The increased accumulation of PAT1-GUS mRNA in pAR209 lines relative to the pAR208 lines could be due to elevated transcription of the transgene or to greater mRNA stability. Thus, nuclear run-on analysis was used to ascertain whether the transgenic lines differed in the rate of transcription. RNA synthesized in vitro by nuclei isolated from pAR208 transgenic line 1–1, pAR209 line 2–1, a line transformed with pBI121, and untransformed plants was used to probe filters to which several genomic DNAs had been affixed by slot blot. The hybridization of radiolabeled RNA to an excess of a cloned gene should be proportional to the rate at which that gene is transcribed in the isolated nuclei. PAT1, TSB1, and CYX1 (an Arabidopsis homolog of the yeast L29 ribosomal protein gene; R. L. Last, unpublished data) should be transcribed at the same rate in all lines and served as hybridization standards, while the vector pBluescript KS(+) was a negative control for non-specific hybridization. As shown in FIG. 6, RNA synthesized by wild-type, pAR208 and pAR209 nuclei hybridize equally to the PAT1, TSB1, and CYX1 DNAs, confirming that equivalent amounts of labeled RNA were used in each hybridization. The signal obtained with GUS DNA is slightly stronger with RNA from the pAR209 line than from the pAR208 plants, indicating a slightly higher rate of fusion gene transcription in the pAR209 line. However, quantitation of the hybridization signal revealed that this difference is less than twofold and is not large enough to explain the difference in mRNA accumulation between these two lines. Therefore, the fusion constructs are transcribed at comparable rates in pAR208 and pAR209 lines, but PAT1-GUS mRNA fails to accumulate in pAR208 lines. This implies that the sequences present in pAR209 but lacking in pAR208 are important for RNA maturation or stability.

In addition to hybridizing very strongly to the GUS gene (FIG. 6), RNA synthesized by nuclei from the pBI121 line hybridized to the vector DNA negative control. It also showed more hybridization to the PAT1, TSB1, and CYX clones than did RNA from the other lines, even though an equal number of counts of radioactive RNA were used in each hybridization. These results are probably due to the 585 bp of M13 sequences including the lacI gene that lie immediately downstream of the nopaline synthase terminator at the 3' end of the GUS gene in pBI121 (Fray et al., 1994). All of the plasmids used in FIG. 6 contain lacI, and the observed hybridization to the negative control and the additional hybridization to all of the other DNAs could be accounted for if 15% of the GUS transcripts extend beyond the nopaline synthase terminator into lacI sequences.

II. DNA Sequences

Many different DNA compositions may be used for delivery to recipient plant cells to ultimately produce fertile transgenic plants having an enhanced expression of desired exogenous protein in accordance with the present invention. For example, DNA segments in the form of vectors and plasmids, or linear DNA fragments, in some instances containing only the DNA element to be expressed in the plant, and the like, may be employed.

Vectors, plasmids, cosmids, YACs (yeast artificial chromosomes) and DNA segments for use in transforming such cells will, of course, generally comprise the cDNA, gene or genes which one desires to introduce into the cells. These DNA constructs will include at least one of the first two introns of the PAT1 gene for generating significant or enhanced expression of the desired gene or genes and will often be made using the XbaI site introduced after the 8th codon of exon 3, or the PstI sites used to make the modified intron 1 (SEQ ID NO:4–6). These DNA constructs can further include structures such as promoters, enhancers, polylinkers, or even regulatory genes as desired. The DNA segment or gene chosen for cellular introduction will often encode a protein of pharmacological interest which will be expressed in the resultant recombinant cells, such as will result in a significant expression of the protein in the plant so that when administered an immune response results. However, this may not always be the case, and the present invention also encompasses transgenic plants incorporating non-expressed transgenes.

A. Regulatory Elements

The construction of vectors which may be employed in conjunction with the present invention will be known to those of skill of the art in light of the present disclosure (see e.g., Sambrook et al., 1989; Gelvin et al., 1990). Preferred constructs will generally include a promoter active in plants such as the CaMV 35S promoter (Odell et al., 1985), or others such as CaMV 19S (Lawton et al, 1987), nos (Ebert et al., 1987), Adh (Walker et al., 1987), sucrose synthase (Yang & Russell, 1990), a-tubulin, actin (Wang et al., 1992), cab (Sullivan et al., 1989), PEPCase (Hudspeth & Grula, 1989) or those associated with the R gene complex (Chandler et al., 1989). Tissue specific promoters such as root cell promoters (Conkling et al., 1990) and tissue specific enhancers (Fromm et al., 1989) are also contemplated to be particularly useful, as are inducible promoters such as ABA-, auxin-, and turgor-inducible promoters. Of course, it is further contemplated that the PAT1 promoter itself would be useful in that it seems to give rise to high level expression throughout the plant, which is often desired.

Constructs will also include, fused to the desired promoter, a DNA construct of the invention including intronic sequences of the PAT1 gene as described above. It is contemplated that any of the promoters listed, and other such promoters as are known in the art, will work in conjunction with the present invention. Preferred promoters for use in conjunction with the present invention include, but are not limited to the CaMV 35S promoter and the PAT1 promoter.

It is also contemplated that tissue specific expression may be functionally accomplished by introducing a constitutively expressed gene (all tissues) in combination with an antisense gene that is expressed only in those tissues where the gene product is not desired.

A particular embodiment of the present invention concerns the fusion of the exogenous protein gene one desires to express to the chloroplast transit peptide-encoding region of the PAT1 gene. In preferred embodiments of this aspect of the invention, the nucleotide sequence encoding the transit peptide includes intron 1 or intron 2 of the PAT1 gene. Evidence suggests that targeting a protein to the chloroplast helps to increase the level of expression achieved, possibly by sequestering a protein that might be toxic if allowed to accumulate in the cytoplasm. For example, pAR254 (with transit peptide, no introns) gives roughly 4 times more GUS activity that pAR208 (no transit peptide, no introns).

It is also contemplated that it may be useful to target the transforming DNA to enter the nucleus, or to promote the integration of the transgene to a particular site in the genome. For example, it may be useful to target introduced DNA to the nucleus as this may increase the frequency of transformation. Within the nucleus itself it would be useful to target a gene in order to achieve site-specific integration. For example, it would be useful to have an gene introduced through transformation replace an existing gene in the cell.

B. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extension or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Elements of the present disclosure are exemplified in detail through the use of the GUS gene, and also through the use of various other markers. Of course, in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the enhancement or increased expression of any gene, including marker genes, into a recipient cell to generate a transformed plant.

1. Selectable Markers

Possible selectable markers for use in connection with the present invention include, but are not limited to neo (aka nptII, or kan), bar, hyg, mutant arDA, methotrexate resistant DHFR, and dalapon dehalogenase.

2. Screenable Markers

Screenable markers that may be employed include a β-glucuronidase or uidA gene (GUS) which encodes an enzyme for which various chromogenic substrates are known, R-locus, β-lactamase, XylE, α-amylase, tyrosinase, β-galactosidase, lux, aequorin and GFP.

C. Transgenes for Enhanced Expression

A particularly important advance of the present invention is that it provides methods and compositions for the increased expression in plant cells of genes in addition to, or other than, marker genes. The transgenes include at least one of the first two introns of the PAT1 gene and are fused or operatively linked to a DNA segment encoding the protein one desires to significantly express. Thus, such transgenes will often be genes that direct the expression of a particular protein or polypeptide product, but they may also be non-expressible DNA segments, e.g., transposons such as Ds that do not direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

In certain embodiments of the present invention, the genes for which enhanced expression is desired will be genes of pharmacological interest. For example, the Hepatitis B Surface Antigen (HBsAg) may be expressed in food plants such as banana, potato, or tomato in such an amount as to cause an immune response in those to whom it is administered. Other such genes for which expression may be enhanced include genes encoding the E. coli heat-labile enterotoxin B subunit, the Norwalk virus capsid protein, the HIV gag protein, and the Schistosoma 28 Kd glutathione-S-transferase. The choice of the particular DNA segments to be delivered to the recipient cells will often depend on the purpose of the transformation.

III. Expression Vectors

The present invention generally involves the use of expression vectors to facilitate the expression of desired exogenous protein genes in plant cells. An expression vector is a vector which is constructed to contain a gene which is to be expressed in a foreign host cell. The construction of expression vectors is a technique which is known in the art.

In general, the expression vectors of the present invention include a promoter such as the CaMV 35S promoter, or others such as CaMV 19S, nos, Adh, sucrose synthase, α-tubulin, actin, cab, PEPCase or those associated with the R gene complex. Inducible promoters such as ABA-, auxin-, and turgor-inducible promoters are also contemplated to be particularly useful. As the enhancement of the expression of the desired protein gene by either of the PAT1 introns appears to be post-transcriptional, it is contemplated that any known plant promoters could be used in conjunction with the present invention.

The expression vectors of the present invention further comprise intronic portions of the PAT1 gene. The inventors have discovered that inclusion of at least one of the first two introns of the PAT1 gene causes increased expression of the desired protein gene.

IV. Usefulness of the Transgenic Plants

The inventors contemplate that the introns incorporated into the expression vectors will cause increased expression of protein genes of desired characteristics in plants. More specifically, the transgenes of the invention containing intronic sequences will increase expression of important protein genes in food plants. Food plants contemplated for use in conjunction with the invention include banana plants, potato plants, maize plants, wheat plants, and tomato plants.

In certain aspects, it is contemplated that the protein genes to be expressed in the food plants will be genes of pharmacological interest such as those listed in Table 2 (page 11). One example of a protein of pharmacological interest to be expressed in food plants is the Hepatitis B Surface Antigen (HBsAg). It has been discovered that transgenic plant tissue expressing this antigen provoked an immune response in mice when the tissue (raw potato tuber) was fed uncooked. Enhancing expression of this antigen in plant material using the introns of the invention should provide an immune response of even greater magnitude. Thus, the methods of the invention can be used to produce "edible vaccines," a conceptually new approach to wide scale immunization.

The concept that adequate tissue levels of recombinant antigens can be achieved in transgenic plants to cause an oral immune response by simple feeding has been supported by two recent studies. Feeding of potatoes which expressed either of two antigens-the heat labile binding subunit of the *E.coli* enterotoxin (LT-B) or the capsid protein of Norwalk virus-to mice caused the animals to develop both serum and mucosal antibodies specific for the respective antigen. Both of these antigens were previously known to be oral immunogens. Although HBsAg is not known as an active oral immunogen, it is contemplated that significant levels of HBsAg will elicit an equivalent immune response. In this respect, it is pertinent to note from earlier studies that the HBsAg in plant cells is present in virus-like-particles; these may increase the likelihood of an interaction with lymphoid tissues in the gut.

V. DNA Delivery

Following the generation of recipient cells, the present invention generally next includes steps directed to introducing an exogenous DNA segment, such as a cDNA or gene, into a recipient cell such that expression of that DNA segment is enhanced. The methods and vectors of the invention are capable of causing expression in cells from virtually any plant species. These cells can in turn be developed into transgenic plants wherein the desired exogenous protein gene introduced exhibits increased expression.

There are many methods for introducing transforming DNA segments into cells, but not all are suitable for delivering DNA to plant cells. Suitable methods are believed to include virtually any method by which DNA can be introduced into a plant cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, by the root explant method, etc.

A. Agrobacterium-mediated transformation

*Agrobacterium tumefaciens* is capable of transferring a segment of DNA (T-DNA) from a Ti plasmid into plant cells. The DNA of interest can be included within the T-DNA and it will become integrated into the plant genomic DNA. There are two preferred methods of using Agrobacterium tumefaciens to introduce a desired DNA into plant cells. The first is the root explant method, which involves treating sections of roots with hormones to induce the formation of callus tissue, exposing that callus to a culture of Agrobacterium, treating the transformed callus with a series of hormones to initiate the formation of shoots, and then inducing those shoots to grow roots. These plantlets are transplanted to soil and the seeds collected for further analysis. The other method is vacuum infiltration. This involves immersing whole, flowering plants in a suspension of Agrobacterium cells, subjecting the submerged plants to a vacuum, and subsequently allowing the plants to recover and set seeds. In both methods, the seeds are screened for those that contain the marker gene present in the T-DNA.

B. Electroporation

Where one wishes to introduce DNA by means of electroporation, it is contemplated that the method of Krzyzek et aL (U.S. Ser. No. 07/635,279 filed Dec. 28, 1990, incorporated herein by reference) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

C. Particle Bombardment

This technique involves coating tungsten or gold microparticles with the DNA of interest. The DNA coated particles are then accelerated by some means, such as a gunpowder charge, sudden release of pressurized helium, or steam vaporized from a drop of water by electric arc, and the microparticles bombard the plant tissue. The particles carry the DNA across the cell wall and release some of it inside the cell, where it can become stably incorporated into the plant genome or can be transiently expressed. The bombardments must be done in a vacuum so that the microparticles are not impeded by the viscosity of the air. The plant tissue can be leaf tissue, meristems, cultured cells, callus, or embryonic tissue.

VI. Production and Characterization of Stable Transgenic Food Plants After effecting delivery of exogenous DNA to recipient cells by any of the methods discussed above, the next steps of the invention generally concern identifying the cells exhibiting enhanced expression for further culturing and plant regeneration. As mentioned above, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene.

A. Selection

An exemplary embodiment of methods for identifying transformed cells involves growing the callus, shoots, or seedlings on medium which contains kanamycin. Transformed seedlings are green and form true leaves and roots in the presence of kanamycin, in contrast to untransformed seedlings which turn white and are severely inhibited in leaf and root formation. Similarly, only transformed callus and shoot material will turn green and continue to develop when grown on medium containing kanamycin.

It is further contemplated that combinations of screenable and selectable markers will be useful for identification of transformed cells. In this way, transformants from cell or tissue types that are not amenable to selection alone may be recovered.

B. Regeneration and Seed Production

Cells that survive the exposure to the selective agent, or cells that have been scored positive in a screening assay, may be cultured in media that supports regeneration of plants. Tissue is preferably maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are transferred every two weeks on this medium. Shoot development will signal the time to transfer to medium lacking growth regulators or containing hormones to induce root formation.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber at about 85% relative humidity, 600 ppm $CO_2$, and 25–250 microeinsteins $m^{-2}xs^{-1}$ of light. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con®s. Regenerating plants are preferably grown at about 19° to 28° C. After the regenerating plants have reached the stage of shoot and root development, they may be transferred to a greenhouse for further growth and testing.

Progeny may be recovered from the transformed plants and tested for expression of the exogenous expressible gene by localized application of an appropriate substrate to plant parts such as leaves.

C. Characterization To confirm the presence of the exogenous DNA or "transgene(s)" in the regenerating plants, a variety of assays may be performed. Such assays include, for example, "molecular biological" assays, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the exogenous gene through the use of techniques well known to those skilled in the art. Note, that intact sequences will not always be present, presumably due to rearrangement or deletion of sequences in the cell.

The enhancement of the presence of DNA elements introduced through the methods of this invention may be determined by polymerase chain reaction (PCR). Using this technique discreet fragments of DNA are amplified and detected by gel electrophoresis. This type of analysis permits one to determine whether a gene is present in a stable transformant, but does not prove integration of the introduced gene into the host cell genome. It is believed in the art, however, that DNA has been integrated into the genome of all transformants that demonstrate the presence of the gene through PCR analysis. In addition, it is not possible using PCR techniques to determine whether transformants have exogenous genes introduced into different sites in the genome, i.e., whether transformants are of independent origin. It is contemplated that it would be possible using PCR techniques to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a gene.

Whereas DNA analysis techniques may be conducted using DNA isolated from any part of a plant, RNA will only be expressed in particular cells or tissue types and hence it will be necessary to prepare RNA for analysis from these tissues. PCR techniques may also be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature and amount of the RNA product may be obtained by Northern blotting. This technique will demonstrate the presence of an RNA species, give information about the integrity of that RNA, and provide a more accurate quantitation of RNA produced from the introduced gene than the PCR techniques. The presence or absence of an RNA species can also be determined using dot or slot blot Northern hybridizations. These techniques are modifications of Northern blotting and will only provide an estimate of the amount of an RNA species.

2. Enhanced Gene Expression

While Southern blotting and PCR may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Expression of PAT1-GUS Fusions

Two translational fusions of the PAT1 promoter to the GUS gene were created, as shown in FIG. 1, to test the influence of downstream sequences on expression, and to control for effects of the PAT1 transit peptide on fusion protein activity. These two constructs differ only in the amount of the PAT1 transcribed region included: pAR208 contains the first 10 codons of PAT1, while pAR209 includes all of exons 1 and 2, the first two introns, and 8 codons of exon 3. The sequences of these two constructs are represented in SEQ ID NO:18 and SEQ ID NO:19, respectively. The 118 amino acids of PAT1 in pAR209 contain the entire chloroplast transit peptide, and presumably include a portion of the $NH_2$-terminus of the mature PAT1 protein.

The fusions in pAR208 and pAR209 were introduced into wild-type Arabidopsis by Agrobacterium tumefaciens-mediated transformation, and the pattern of GUS expression was determined by histochemical staining. As might be expected for fusions to the promoter of a gene that encodes a "housekeeping" enzyme, transgenic plants transformed with pAR209 (henceforth called pAR209 lines) show intense staining in virtually all parts of the plants, as seen in FIG. 2E–FIG.2H. The strong GUS activity in tissues that lack chloroplasts (such as roots) indicates that expression of PAT1 is not limited to photosynthetically active cells, and suggests that the PAT1 transit peptide can direct the import of proteins into plastids other than chloroplasts. In contrast to the widespread staining of pAR209 lines, plants transformed with pAR208 (pAR208 lines) show weak histochemical staining only in the root tips and at the base of the leaf petioles (FIG. 2A–FIG.2D) in a pattern similar to that seen from TSB1-GUS fusions (Pruitt and Last, 1993).

Two lines of evidence suggest that the difference in GUS activity observed in pAR208 and pAR209 lines is quantitative. First, those tissues that show any histochemical staining in pAR208 lines, such as root tips and the base of immature seed pods (FIG. 2B and FIG. 2D), are the regions of most intense staining in pAR209 lines (FIG. 2F and FIG. 2H). Furthermore, the staining observed in pAR209 lines treated very briefly with chromogenic substrate resembles the pattern of pAR208 lines stained for a longer time (data not shown).

Example 2

Role of Introns

While the above results indicate a role for transcribed sequences in post-transcriptional regulation of PAT1-GUS, they do not indicate whether the effects are mediated by intronic or coding sequences. This question was addressed by constructing derivatives of pAR209 lacking either the first, second, or both introns (constructs are shown in FIG. 7). These GUS fusions (pAR252, pAR253, and pAR254, respectively) were each introduced into wild-type Arabidopsis plants in two independent transformation experiments. Lines that segregate as if the transgene was integrated at a single locus were identified by segregation of kanamycin-resistance in self-cross progeny, and GUS activity was assessed by histochemical staining and enzyme assays.

The data shown in Table 3 are consistent with the hypothesis that the presence of a single intron is sufficient for full GUS expression. Most plants transformed with pAR253 (containing the first PAT1 intron only) or pAR252 (containing only the second intron) have high levels of GUS enzyme activity, with mean GUS activity that is similar to the positive control pAR209 line 2–1. Furthermore, the patterns of histochemical staining of representative pAR252 and pAR253 lines resemble those of the pAR209 lines, as seen in FIG. 8. In contrast, the six pAR254 transgenic lines tested have a low level of GUS enzyme activity, averaging 18% of the activity of pAR209 line 2–1 (Table 3) and weak histochemical staining in a pattern that is reminiscent of that seen in pAR208 lines (compare FIG. 2A and FIG. 2B with FIG. 8C and FIG. 8F). Therefore, fusions containing one or both PAT1 introns are expressed at a much higher level than fusions lacking introns, and this suggests that the introns are the main cause of the difference in GUS expression between the pAR208 and pAR209 lines.

TABLE 3

RELATIVE GUS ACTIVITY OF pAR252,
pAR253, and pAR254 TRANSGENIC LINES[a,b]

| pAR252 Line | GUS Activity | pAR253 Line | GUS Activity | pAR254 Line | GUS Activity |
|---|---|---|---|---|---|
| A3 | 115 | A2 | 276 | A1 | 11 |
| A6 | 86 | A4 | 213 | B1 | 44 |
| A8 | 44 | A5 | 96 | B4 | 5 |
| A9 | 150 | A7 | 116 | B5 | 12 |
| A13 | 224 | B1 | 258 | B6 | 20 |
| A14 | 1 | B2 | 257 | B8 | 14 |
| A15 | 46 | B4 | 121 | | |
| A19 | 104 | B5 | 62 | | |
| A20 | 55 | B9 | 75 | | |
| B2 | 217 | | | | |
| Average | 104 ± 71 | Average | 164 ± 81 | Average | 18 ± 13 |

[a]Lines designated A or B are from different transformations and therefore must be independent.
[b]GUS enzyme activity is expressed as a percentage of that observed for pAR209 line 2-1, which averaged 5,590 ± 850 pmoles methylumbelliferone $min^{-1}$ mg $protein^{-1}$ when assayed on five different days.

Example 3

Plasmid Construction

The plasmids used in this invention are described in Table 4. Promoter fragments of PAT1 were generated from pAR167 by PCR using a vector primer and oligonucleotide OAR2 (5'-GATAA TCTAGAGCTCGTCGTCGCC-3') (SEQ ID NO:16) or OAR3 (5'-GTTGC TCTAGACCGATCAATCAAGG-3') (SEQ ID NO:17), which introduce an XbaI site (underlined) after PAT1 codons 10 and 118 respectively. The resulting XbaI fragments were inserted into the XbaI site of pAR183 between an additional 1.2 kb of distal PAT1 flanking sequences and the GUS gene with the GUS ATG converted to CTG (Pruitt and Last, 1993), creating pAR200 and pAR201. The structure of the junctions was confirmed by sequencing, and the resulting fusions were inserted as KpnI fragments into the binary vector pEND4K (Klee et al., 1985) to generate pAR208 and pAR209 (FIG. 1).

Derivatives of pAR209 lacking the first, second, or both introns, were constructed by using a HindIII site in exon 1 and an NheI site in exon 2 as follows (see FIG. 7). Oligonucleotide OAR3 and a vector primer were used to PCR amplify the region encoding the presumed chloroplast transit peptide from a PAT1 cDNA clone, pAR129, and a PAT1 genomic clone, pAR167. The 309 bp HindIII-XbaI product from pAR129 and the 771 bp HindIII-XbaI product from pAR167 were subcloned into pBluescriptKS(+) to make pAR229 and pAR230 respectively. Exchanging the 252 bp HindIII-NheI fragment of pAR229 with the corresponding 362 bp HindIII-NheI fragment from pAR230 gave plasmids pAR231 and 232. The HindIII site of each insert was used to reconstruct the 2.4 Kb PAT1 promoter, and the XbaI site was used to generate translational fusions to GUS as described above for pAR208 and pAR209. The PAT1 promoter:GUS:nopaline synthase terminator fragments were inserted into the KpnI site of pEND4K to generate plasmids pAR252, pAR253, and pAR254.

TABLE 4

PLASMIDS USED IN THIS INVENTION

| Name | Description |
| --- | --- |
| pAR125 | A 4.1 kb SalI-BamHI PAT1 genomic fragment in pGEM7Zf(+) (Promega) (Rose et al., 1992). |
| pAR129 | A 1.6 Kb PAT1 cDNA extending 21 bp upstream of the start of translation as an XhoI fragment in the XhoI site of pBluescript KS(+) (Stratagene). |
| pAR140 | The 3.0 kb HindIII-EcoRI 35S:GUS:NOS fragment from pBI121 (Clontech) in the HindIII-EcoRI sites of pBluescript KS(+). |
| pAR152 | The 1.9 kb BamHI-SacI GUS fragment from pBI121 in the BamHI-SacI sites of pBluescript KS(+). |
| pAR167 | A 4.1 kb SalI-BamHI PAT1 genomic fragment in the XhoI-BamHI sites of pGEM7Zf(+). |
| pAR170 | A 1.2 kb KpnI-SalI partial digestion product containing sequences 5' to PAT1 in the KpnI-XhoI sites of pBluescript KS(+). |
| pAR183 | The 2.2 kb XbaI-XhoI fragment containing the ATG-less GUS gene and nopaline synthase terminator from pCTGus (Pruitt and Last, 1993) in the XbaI-XhoI sites of pAR170. |
| pAR200 | A 1.2 kb XbaI fragment from PCR amplification of the PAT1 promoter from pAR167 using oligonucleotide OAR2 in the XbaI site of pAR183. |
| pAR201 | A 2.0 kb XbaI fragment from PCR amplification of the promoter, first two exons, and first two introns of PAT1 from pAR167 using oligonucleotide OAR3, in the XbaI site of pAR183. |
| pAR208 | The 4.6 kb KpnI fragment of pAR200 in the KpnI site of pEND4K. |
| pAR209 | The 5.4 kb KpnI fragment of pAR201 in the KpnI site of pEND4K. |
| pAR229 | A 309 bp HindIII-XbaI fragment from PCR amplification of pAR129 using oligonucleotide OAR3 in the HindIII-XbaI sites of pBluescript KS(+). |

TABLE 4-continued

PLASMIDS USED IN THIS INVENTION

| Name | Description |
| --- | --- |
| pAR230 | The 771 bp HindIII-XbaI fragment from pAR201 in the HindIII-XbaI sites of pBluescript KS(+). |
| pAR231 | The 252 bp HindIII-NheI fragment from pAR229 in the HindIII-NheI sites of pAR230. |
| pAR232 | The 362 bp HindIII-NheI fragment from pAR230 in the HindIII-NheI sites of pAR229. |
| pAR252 | Derivative of pAR231. Identical to pAR209 except that the first intron of PAT1 is deleted. |
| pAR253 | Derivative of pAR232. Identical to pAR209 except that the second intron of PAT1 is deleted. |
| pAR254 | Derivative of pAR229. Identical to pAR209 except that the first and second introns of PAT1 are deleted. |
| pMBT2 | A 4.2 kb EcoRI TSB1 genomic fragment in pUC118 (Berlyn et al., 1989). |
| pRLB453 | A 0.7 kb BamHI-EcoRV cDNA containing the Arabidopsis cDNA CYX that encodes a protein with homology to the Saccharomyces cerevisiae L29 ribosomal protein (R.L. Last, unpublished data) in pGEM3Z. |

Example 4

Plant Transformation and Growth

Plasmids used in transformations were electroporated into *Agrobacterium tumefaciens* strain LBA4404. The resulting strains were used to transform wild-type *Arabidopsis thaliana* ecotype Columbia by the root explant method (Rose et al., 1992). The Arabidopsis ecotype C24 transformed with pBI121 (Clontech) served as a positive control for GUS expression.

Plants were grown on PNS agar medium (Haughn and Somerville, 1986) or in Cornell mix (Landry et al., 1995) under continuous light. Histochemical staining of plants with 5-bromo-4-chloro-3-indolyl b-D-glucuronide (X-Gluc), and quantitative fluorometric assays using 4-methylumbelliferyl glucuronide (MUG), were performed as described (Pruitt and Last, 1993). Protein concentrations were determined using the Biorad dye-binding kit, with IgG as a standard.

Example 5

Molecular Analysis

Genomic DNA and RNA blots were performed using standard techniques as described in Rose et al., 1992 and in Pruitt and Last, 1993. Proteins were extracted, separated by polyacrylamide gel electrophoresis, and transferred to nitrocellulose membranes as described in Zhao and Last, 1995. The membranes were incubated with rabbit polyclonal anti-GUS antibodies (created by Dr. T. McKnight, a gift from Dr. John Steffens), which were detected using $^{125}$I-protein A. Radioactivity was quantitated using a PhosphorImager (Molecular Dynamics model #400A, Sunnyvale, Calif.).

Example 6

Nuclear Run-ons

Nuclei were isolated from 50 g of leaves from 3-week old Arabidopsis plants using a published procedure (Feinbaum and Ausubel, 1988) and were stored at −70° C. until used. The yield of nuclei was estimated by staining with DAPI and counting under a fluorescence microscope using a haemocytometer. Approximately $2 \times 10^7$ nuclei were thawed on ice, collected by a brief centrifugation, and resuspended in 100 μl NSB (50% glycerol, 20 mM HEPES pH 7.2, 5 mM MgCl$_2$, 2 mM dithiothreitol) and 100 μl 2X reaction buffer (10 mM Tris pH 7.5, 5 mM MgCl$_2$, 4 mM MnCl$_2$, 300 mM KCI, 8 mM dithiothreitol, 0.6 mM ATP, 0.6 mM CTP, 0.6 mM GTP, and 15 μM UTP). Transcription was performed as described in Ausubel et al., 1993 except that 125 μCi of α-$^{32}$P-UTP (800 Ci/mMol, Amersham) was used in each sample and the NaOH hydrolysis step was omitted. 10$^7$ cpm of RNA from each sample was hybridized for 72 hrs at 65° C. to nitrocellulose strips to which 10 μg of each of the following linearized, denatured plasmids had been slot-blotted; pBluescript KS(+), pMBT2 (TSB1), pAR125 (PAT1), pAR152 (GUS), and pRLB453 (CYX).

Example 7

Identification of Independent Lines

To test the possibility that the observed difference in histochemical staining pattern between pAR208 and pAR209 lines was due to differences in expression caused by the chromosomal context into which each transgene integrated (position effect; Peach and Velten, 1991), multiple pAR208 and pAR209 lines were isolated. The segregation ratios of progeny from kanamycin-resistant plants were used to identify lines that contain the transgene at a single locus. Homozygous single-locus lines were then screened by genomic DNA blots to demonstrate that these lines arose from independent transformation events and that each contained a single unrearranged copy of the transgene. This analysis was facilitated by the BamHI site at the 5' end of the GUS gene in both pAR208 and pAR209 (FIG. 1): the size of the GUS-containing genomic fragment is a function of how far from a BamHI site the transgene integrates, and lines with different sized BamHI fragments are independent. Furthermore, because each separate integration should give a different sized junction fragment, the number of bands in each lane indicates the number of transgene inserts.

Four pAR208 lines and six pAR209 lines were identified that contain single and unique sites of transgene insertion, as shown in FIG. 3A. The distinct size of the GUS-hybridizing BamHI fragment from each line shows that all are independent transformants. One discrete band is observed in most lanes, confirming that a single transgene is present in each line. The smear of hybridization in lanes from pAR208 line 1–4 and pAR209 line 1–35 could be explained if the GUS-containing BamHI fragment is very large, because it would be susceptible to shearing during DNA isolation and may also transfer poorly to the membrane.

FIG. 3B shows that each pAR208 and pAR209 line contains an additional PAT1 promoter fragment of the size expected for an unrearranged insertion of the transgene. Each pAR208 and pAR209 line contains a 2.4 kb or 3.2 kb BamHI fragment respectively, which corresponds to the size of the PAT1 promoter fragment in the pAR208 and pAR209 plasmids (FIG. 1). The endogenous PAT1 gene is on a 6.3 kb BamHI fragment, seen in all transgenic lines and wild-type plants. The similar band intensities of the endogenous and transgenic PAT1 fragments is further evidence that each line contains a single transgene.

Example 8

Quantitation of GUS Enzyme Activity

To quantitate the difference between pAR208 and pAR209 lines, the GUS enzyme activity in extracts of leaf tissue from 3-week-old plants was determined using the quantitative 4-methylumbelliferylglucuronide assay (Jefferson et al., 1987). As shown in Table 5, all of the pAR209 lines had high levels of GUS activity that were remarkably similar, each within 20% of the mean. Surprisingly, a positive control line containing three copies of pBI121, a transcriptional fusion in which the GUS gene is under control of the cauliflower mosaic virus 35S promoter, showed only twice as much GUS activity as did the pAR209 lines. Three of the pAR208 lines had similar low but detectable GUS activities that averaged ~4% of those seen in the pAR209 lines. The fourth pAR208 line (1–6) had as little GUS activity as untransformed plants, and may contain a transgene that was inactivated by mutation or that cannot be expressed due to the chromosomal location into which it integrated. Because multiple independent lines homozygous for single transgenes gave similar results, it is highly unlikely that position effects account for the difference between pAR208 and pAR209 lines. Therefore, the different GUS activities of these lines is almost certainly a result of differences between the transgenes themselves.

TABLE 5

QUANTITATION OF GUS ACTIVITY IN TRANSGENIC LINES

| Transgene | Line | GUS Activity[a] |
| --- | --- | --- |
| None | Wild-type | 11 ± 2 |
| pAR208 | 1-1 | 240 ± 40 |
|  | 1-4 | 180 ± 110 |
|  | 1-6 | 14 ± 4 |
|  | 1-23 | 300 ± 10 |
|  | Average | 180 ± 110 |
| pAR209 | A4-1 | 5,300 ± 190 |
|  | 2-1 | 5,750 ± 550 |
|  | 1-2 | 5,750 ± 560 |
|  | 1-11 | 6,440 ± 300 |
|  | 1-13 | 4,900 ± 160 |
|  | 1-35 | 4,390 ± 60 |
|  | Average | 5,420 ± 660 |
| pBI121 |  | 10,600 ± 1,140 |

[a]Mean activity of three extracts ± standard deviation.
Units = pmoles methylumbelliferone min$^{-1}$ mg protein$^{-1}$.

Example 9

Detection of Fusion Protein

One hypothesis to explain the higher GUS activity of pAR209 lines is that the fusion protein encoded by pAR209 could be more catalytically active than that derived from pAR208 due to subcellular localization or the influence on enzyme activity of the PAT1 residues that remain fused to GUS after transit peptide cleavage. Previous studies have shown that the GUS protein remains functional when directed into chloroplasts by a transit peptide (Klosgen et al., 1989; Klosgen and Weil, 1991; Russell et al., 1993) even with up to 58 foreign residues fused to the NH2-terminus of GUS (Kavanagh et al., 1988).

To investigate the possibility that the pAR208 and pAR209 plants produce equivalent levels of fusion protein with different enzymatic activities, the amount of fusion protein in each of the independent lines was measured by probing protein blots with anti-GUS antibodies. Proteins recognized by the anti-GUS antibodies were readily detected at similar levels in all of the pAR209 lines but were not detected in any of the pAR208 lines, as shown in FIG. 4. Therefore, the pAR208 and pAR209 lines produce different quantities of fusion protein, and this difference is sufficient to explain the GUS enzymatic activity of each line.

Even though the precise PAT1 transit peptide cleavage site is not known, the data presented in FIG. 4 can be used to estimate its approximate location. The fusion protein encoded by pAR209 migrates in an SDS polyacrylamide gel as if it were approximately 5 kd larger than the GUS protein encoded by pBI121 (FIG. 4). However, this difference in migration is less than the 13 kd difference predicted if the entire transit peptide remained fused to GUS. This suggests that ~80 of the $NH_2$-terminal PAT1 residues are removed by chloroplast signal peptidase, leaving roughly 40 residues of PAT1 and 10 amino acids encoded by linker sequences fused to GUS in the mature fusion protein.

Example 10

Accumulation of PAT1-GUS MRNA

The difference in fusion protein accumulation between pAR208 and pAR209 lines could be due to unequal mRNA accumulation, translation, or fusion protein stability. To differentiate between these possibilities, RNA gel blots from each of the lines were hybridized with the GUS gene. As shown in FIG. 5A, MRNA that hybridized to the GUS probe was readily detected in all of the pAR209 lines, but was not seen in RNA from pAR208 lines. The ethidium-stained gel (FIG. 5B) confirms that equivalent amounts of RNA are present in each lane. Therefore, the pAR208 and pAR209 lines differ in the accumulation of PAT1-GUS mRNA, and this corresponds to the difference between these lines in fusion protein accumulation and GUS enzyme activity.

The positive control pBI121 line contained such high levels of GUS RNA that a hybridization signal comparable to those from the pAR209 lines was achieved only when a fraction as much pBI121 total RNA was loaded (FIG. 5). Quantitation of radioactivity revealed that the pBI121 line accumulated approximately 175 times more GUS-hybridizing mRNA than the pAR209 lines.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ausubel et al., *Current Protocols in Molecular Biology*, (Suppl. 26), 1993.

Baker, Wilhelm, and Thomashow, "The 5'-region of Arabidopsis thaliana corl5a has cis-acting elements that confer cold-, drought- and ABA-regulated gene expression," *Plant Molecular Biology*, 24:701–703, 1994.

Berget, Moore, and Sharp, "Spliced segments at the 5' terminus of adenovirus 2 late mRNA," *Proc. Natl. Acad. Sci. USA*, 74(8):3171–3175, August 1977.

Berlyn, Last, and Fink, "A gene encoding the tryptophan synthase β subunit of Arabidopsis thaliana," *Proc. Natl. Acad. Sci. USA*, 86:4604–4608, June, 1989.

Buchman and Berg, "Comparison of Intron-Dependent and Intron-Independent Gene Expression," *Molecular and Cellular Biology*, 8(10):4395–4405, October, 1988.

Callis, Fromm, and Walbot, "Introns increase gene expression in cultured maize cells," *Genes & Development*, 1:1183–1200, 1987.

Chandler, V. L., Radicella, J. P., Robbins, P. P., Chen, J., Turks, D., *The Plant Cell* 1:1175–1183, 1989.

Chee, Klassy, and Slightom, "Expression of a bean storage protein 'phaseolin minigene' in foreign plant tissues," *Gene*, 41:47–57, 1986.

Chow, Gelinas, Broker, and Roberts, "An Amazing Sequence Arrangement at the 5' Ends of Adenovirus 2 Messenger RNA," *Cell*, 12:1–8, September, 1977.

Clancy, Vasil, Hannah, and Vasil, "Maize Shrunken-1 intron and exon regions increase gene expression in maize protoplasts," *Plant Science*, 98:151–161, 1994.

Conkling, M. A., Cheng, C. L., Yamamoto, Y. T., Goodman, H. M., *Plant Physiol* 93:1203–1211, 1990.

Curie, Axelos, Bardet, Atanassova, Chaubet, and Lescure, "Modular organization and developmental activity of an *Arabidopsis thaliana* EF-1α gene promoter," Mol. Gen. Genet., 238:428–436, 1993.

Curie, Liboz, Bardet, Gander, Medale, Axelos, and Lescure, "Cis and trans-acting elements involved in the activation of *Arabidopsis thaliana* A1 gene encoding the translation elongation factor EF-1α," *Nucleic Acids Research*, 19(6):1305–1310, 1991.

De Almeida, Gossele, Muller, Dockx, Reynaerts, Botterman, Krebbers, and Timko, "Transgenic expression of two marker genes under the control of an Arabidopsis rbcS promoter: Sequence encoding the Rubisco transit peptide increase expression levels," *MoL Gen. Genet.*, 218:78–86, 1989.

Dean, Favreau, Bond-Nutter, Bedbrook, and Dunsmuir, "Sequences Downstream of Translation Start Regulate Quantitative Expression of Two Petunia rbcS Genes," *The Plant Cell*, 1:201–208, February, 1989.

Dickey, Nguyen, Allen, and Thompson, "Light Modulation of Ferredoxin mRNA Abundance Requires an Open Reading Frame," *The Plant Cell*, 6:1171–1176, August, 1994.

Douglas, Hauffe, Ites-Morales, Ellard, Paszkowski, Hahibrock, and Dangl, "Exonic sequences are required for elicitor and light activation of a plant defense gene, but promoter sequences are sufficient for tissue specific expression," *The EMBO Journal*, 10(7):1767–1775, 1991.

Ebert, P. R., Ha, S. B., An. G., *PNAS* 84:5745–5749, 1987.

Evans and Scarpula, "Introns in the 3' untranslated region can inhibit CAT and β-galactosidase gene expression," *Gene*, 84:135–142, 1989.

Feinbaum and Ausubel, "Transcriptional Regulation of the Arabidopsis thaliana Chalcone Synthase Gene," *Molecular and Cellular Biology*, 8(5):1985–1992, May, 1988.

Fray, Wallace, and Grierson, "Identification of unexplained DNA fragments within the T-DNA borders of the Bin 19 plant transformation vector," *Plant Molecular Biology*, 25:339–342, 1994.

Fromm, H., Katagiri, F., Chua, N. H., *The Plant Cell* 1:977–984, 1989.

Gallie, "Posttranscriptional Regulation of Gene Expression in Plants," *Annu. Rev. Plant Physiol. Plant Mol. Biol.*, 44:77–105, 1993.

Gallie, D. R. and Young, T. E., "The regulation of gene expression in transformed maize aleurone and endosperm protoplasts," Plant Physiol., 106:929–939, 1994.

Gelvin, S. B., Schilperoort, R. A., Varma, D.P.S., eds. Plant Molecular Biology Manual, 1990.

Green, "Pre-mRNA splicing," Annu. Rev. Genet., 20:671–708, 1986.

Haughn and Somerville, "Sulfonylurea-resistant mutants of Arabidopsis thaliana," Mol. Gen. Genet., 204:430–434, 1986.

Huang and Gorman, "Intervening sequences increase efficiency of RNA 3' processing and accumulation of cytoplasmic RNA," Nucleic Acids Research, 18(4):937–947, 1990.

Hudspeth, R. L. and J. W. Grula., Plant Mol. Biol. 12:579–589, 1989.

Jefferson, Kavanagh, and Bevan, "GUS fusions: β-glucuronidase as a sensitive and versatile gene fusion marker in higher plants," The EMBO Journal, 6(13):3901–3907, 1987.

Jeffreys and Flavell, "The Rabbit β-Globin Gene Contains a Large Insert in the Coding Sequence," Cell, 12:1097–1108, December, 1977.

Kato, Shirano, Kawazu, Tada, Itoh, and Shibata, "A Modified β-Glucuronidase Gene: Sensitive Detection of Plant Promoter Activities in Suspension-Cultured Cells of Tobacco and Rice," Plant Molecular Biology Reporter, 9(4):333–339, 1991.

Kavanagh, Jefferson, and Bevan, "Targeting a foreign protein to chloroplasts using fusions to the transit peptide of a chlorophyll a/b protein," Mol. Gen. Genet., 215:38–45, 1988.

Klee, Yanofsky, and Nester, "Vectors for Transformation of Higher Plants," Biotechnology, 3:637–642, 1985.

Klosgen and Weil, "Subcellular location and expression level of a chimeric protein consisting of the maize waxy transit peptide and the β-glucuronidase of Escherichia coli in transgenic potato plants," Mol. Gen. Genet., 225:297–304, 1991.

Klosgen, Saedler, and Weil, "The amyloplast-targeting transit peptide of the waxy protein of maize also mediates protein transport in vitro into chloroplasts," Mol. Gen. Genet., 217:155–161, 1989.

Kuhlemeier, Fluhr, and Chua, "Upstream sequences determine the difference in transcript abundance of pea rbcS genes," Mol Gen. Genet., 212:405–41, 1988.

Landry, Chapple, and Last, "Arabidopsis Mutants Lacking Phenolic Sunscreens Exhibit Enhanced Ultraviolet-B Injury and Oxidative Damage," Plant Physiol., 109:1159–1166, 1995.

Larkin, Oppenheimer, Pollock, and Marks, "Arabidopsis GLABROUS1 Gene Requires Downstream Sequences for Function," The Plant Cell, 5:1739–1748, December, 1993.

Last and Fink, "Tryptophan-Requiring Mutants of the Plant Arabidopsis thaliana," Science, 240:305–310, April, 1988.

Lawton, M. A., Tierney, M. A., Nakamura, I., Anderson, E., Komeda, Y., Dube, P., Hoffinan, N., Fraley, R. T., Beachy, R. N., Plant Mol. Biol. 9:315–324, 1987.

Luehrsen and Walbot, "Addition of A- and U-rich sequence increases the splicing efficiency of a deleted from of a maize intron," Plant Molecular Biology, 24:449–463, 1994.

Luehrsen and Walbot, "Intron enhancement of gene expression and the splicing efficiency of introns in maize cells," Mol. Gen. Genet., 225:81–93, 1991.

Maas, Laufs, Grant, Korfhage, and Werr, "The combination of a novel stimulatory element in the first exon of the maize Shrunken-1 gene with the following intron 1 enhances reporter gene expression up to 1000-fold," Plant Molecular Biology, 16:199–207, 1991.

Mascarenhas and Hamilton, "Artifacts in the localization of GUS activity in anthers of petunia transformed with a CaMV 35S-GIS construct," The Plant Journal, 2(3):405–408, 1992.

Niyogi, K., "Molecular and genetic analysis of anthranilate synthase in Arabidopsis thaliana," Ph.D. Dissertation, Massachusetts Institute of Technology, 1993.

Niyogi, Last, Fink and Keith, The Plant Cell, 5:1011–1027, 1993.

Norris, Meyer, and Callis, "The intron of Arabidopsis thaliana polyubiquitin genes is conserved in location and is a quantitative determinant of chimeric gene expression," Plant Molecular Biology, 21:895–906, 1993.

Oard, Paige, and Dvorak, "Chimeric gene expression using maize intron in cultured cells of breadwheat," Plant Cell Reports, 8:156–160, 1989.

Odell, J. T., Nagy, F., Chua, N. H., Nature 313:810–812, 1985.

Omirulleh, S, Abraham, M., Golovkin, M., Stefanov, I., Karabaev, M. K., Mustardy, L., Morocz, S., Dudits, D., Plant Molecular Biology 21:415–428, 1993.

Peach and Velton, "Transgene expression variability (position effect) of CAT and GUS reporter genes driven by linked divergent T-DNA promoters," Plant Molecular Biology, 17:49–60, 1991.

Pruitt and Last, "Expression Patterns of Duplicate Tryptophan Synthase β Genes in Arabidopsis thalianai," Plant Physiol., 102:1019–1026, 1993.

Radwanski, Zhao, and Last, "Arabidopsis thaliana tryptophan synthase alpha: gene cloning, expression, and subunit interaction," Mol Gen. Genet., 248:657–667, 1995.

Rose, Casselman, and Last, "A Phosphoribosylanthranilate Transferase Gene Is Defective in Blue Fluorescent Arabidopsis thaliana Tryptophan Mutants," Plant Physiol., 100:582–592, 1992.

Ruby and Abelson, "An Early Hierarchic Role of U1 Small Nuclear Ribonucleoprotein in Spliceosome Assembly," Science, 242:1028–1035, November, 1988.

Russell, DeBoer, Stark, Preiss, and Fromm, "Plastid targeting of E. coli β-glucuronidase and ADP-glucose pyrophosphorylase in maize (Zea mays L.) cells," Plant Cell Reports, 13:24–27, 1993.

Sambrook, J., Fritsch, E. F., and Maniatus, T., Molecular Cloning, A Laboratory Manual 2nd ed, 1989.

Sistrunk, Antosiewicz, Purugganan, and Braam, "Arabidopsis TCH3 Encodes a Novel $Ca^{2+}$ Binding Protein and Shows Environmentally Induced and Tissue-Specific Regulation," The Plant Cell, 6:1553–1565, November, 1994.

Sullivan and Green, "Post-transcriptional regulation of nuclear-encoded genes in higher plants: the roles of mRNA stability and translation," Plant Molecular Biology, 23:1091–1104, 1993.

Sullivan, T. et al., Mol. Gen. Genet, 215:431–440, 1989.

Uknes, Dincher, Friedrich, Negrotto, Williams, Thompson-Taylor, Potter, Ward, and Ryals, "Regulation of Pathogenesis-Related Protein-1a Gene Expression in Tobacco," The Plant Cell, 5:159–169, February, 1993.

Ulmasov and Folk "Analysis of the Role of 5' and 3' Flanking Sequence Elements upon in Vivo Expression of the Plant $tRNA^{Trp}$ Genes," The Plant Cell, 7:1723–1734, October, 1995.

Vasil, Clancy, Ferl, Vasil, and Hannah, "Increased Gene Expression by the First Intron of Maize Shrunken-1 Locus in Grass Species," *Plant Physiol.,* 91:1575–1579, 1989.

Vaucheret, Marion-Poll, Meyer, Faure, Marin, and Caboche, "Interest in and limits to the utilization of reporter genes for the analysis of transcriptional regulation of nitrate reductase," *Mol. Gen. Genet.,* 235:259–268, 1992.

Walker, J. C., Howard, E. A., Dennis, E. S., Peacock, W. J, *PNAS* 84:6624–6628, 1987.

Wang, Y., Zhang, W., Cao, J., McEhoy, D. and Ray Wu. *Molecular and Cellular Biology* 12: 3399–3406, 1992.

Yang, N. S., Russell, D., *PNAS* 87:4144–4148, 1990.

Zhang, Lawton, Hunter, and Lamb, "atpkl, a Novel Ribosomal Protein Kinase Gene from Arabidopsis," *The Journal of Biological Chemistry,* 269(26):17586–17592, July, 1994.

Zhao and Last, "Immunological Characterization and Chloroplast Localization of the Tryptophan Biosynthetic Enzymes of the Flowering Plant *Arabidopsis thaliana*," The Journal of Biological Chemistry, 270(11) :6081–6087, March, 1995.

---

What is claimed is:

1. A method of increasing exogenous protein expression in a cell, said method comprising the steps of:
   a) constructing a DNA fusion comprising intron 1 or intron 2 of the PAT1 gene operatively linked to a DNA segment from a gene other than the PAT1 gene encoding the exogenous protein one desires to express in the cell; and
   b) introducing said fusion into a host cell so that the cell expresses the fusion.

2. The method of claim 1, wherein said cell is a plant cell.

3. The method of claim 1, wherein said DNA fusion comprises intron 1 of the PAT1 gene.

4. The method of claim 1, wherein said DNA fusion comprises intron 2 of the PAT1 gene.

5. The method of claim 1, wherein said DNA fusion comprises intron 1 and intron 2 of the PAT1 gene.

6. The method of claim 1, wherein said DNA fusion comprises a modified intron 1 of the PAT1 gene having the sequence of SEQ ID NO:4, SEQ ID NO:5, or SEQ ID NO:6.

7. A method of increasing exogenous protein expression in a transgenic plant, said method comprising the steps of:
   a) constructing a DNA fusion comprising intron 1 or intron 2 of the PAT1 gene operatively linked to a DNA segment from a gene other than the PAT1 gene encoding the exogenous protein one desires to express in
   b) the transgenic plant; and
   expressing said fusion in said plant.

8. The method of claim 7, wherein said DNA segment encodes a reporter gene in accordance with Table 1.

9. The method of claim 7, wherein said DNA segment encodes a protein of pharmacological interest.

10. The method of claim 9, wherein said DNA segment encodes an animal vaccine gene in accordance with Table 2.

11. The method of claim 9, wherein said DNA segment encoding exogenous protein encodes a human vaccine gene in accordance with Table 2.

12. The method of claim 11, wherein said DNA segment encodes Hepatitis B surface antigen.

13. The method of claim 7, wherein said plant is further defined as a tobacco plant, a potato plant, a banana plant, a tomato plant, or any member of the plant genus Brassica.

14. The method of claim 13, wherein said plant is further defined as a potato plant.

15. The method of claim 7, wherein said DNA fusion is introduced into said plant by *Agrobacterium tumefaciens*-mediated transformation by vacuum filtration.

16. The method of claim 7, wherein said DNA fusion further comprises a DNA segment encoding an exogenous protein operatively linked to exons 1 and 2, 8 codons of exon 3, and intron 1 or intron 2 of the PAT1 gene.

17. The method of claim 16, wherein said DNA fusion further comprises a DNA segment encoding an exogenous protein operatively linked to exons 1 and 2, 8 codons of exon 3, and intron 1 of the PAT1 gene.

18. The method of claim 16, wherein said DNA fusion further comprises a DNA segment encoding an exogenous protein operatively linked to exons 1 and 2, 8 codons of exon 3, and intron 2 of the PAT1 gene.

19. The method of claim 16, wherein said DNA fusion further comprises a DNA segment encoding an exogenous protein operatively linked to exons 1 and 2, 8 codons of exon 3 and introns 1 and 2 of the PAT1 gene.

20. The method of claim 16, wherein said DNA segment encodes a reporter gene.

21. The method of claim 20, wherein said DNA fusion further comprises a DNA segment is further defined as encoding β-glucuronidase (GUS) reporter gene.

22. The method of claim 21, wherein said GUS reporter gene is derived from pBI101, pBI121, pBI221, or pCTGus.

23. The method of claim 7, wherein said DNA segment encodes a protein of pharmacological interest.

24. The method of claim 23, wherein said DNA segment encodes an animal vaccine gene in accordance with Table 2.

25. The method of claim 23, wherein said DNA segment encodes a human vaccine gene in accordance with Table 2.

26. The method of claim 25, wherein said DNA segment encodes Hepatitis B surface antigen.

27. The method of claim 7, wherein said DNA fusion further comprises a DNA segment encoding an exogenous protein operatively linked to exon 3 and intron 2 of the PAT1 gene.

28. The method of claim 7, wherein said DNA fusion further at least one intron and a DNA segment encoding the entire chloroplast transit peptide of the PAT1 gene.

29. The method of claim 28, wherein said DNA fusion further comprises a DNA segment encoding chloroplast transit peptide of PAT1 is further defined as comprising exon 1 and at least 10 codons of exon 2 of the PAT1 gene.

30. The method of claim 7, wherein said DNA fusion further comprises a DNA segment comprising at least one intron and a DNA segment comprising at least 60 codons of the chloroplast transit peptide of the PAT1 gene.

31. A recombinant vector comprising a DNA segment encoding an exogenous protein gene, other than the product of the PAT1 gene, operatively linked to a gene segment comprising intron 1 or intron 2 of the PAT1 gene.

32. The vector of claim 31, wherein said DNA segment encoding exogenous protein encodes a reporter gene in accordance with Table 1.

33. The vector of claim 32, wherein said DNA segment encoding reporter gene is further defined as encoding β-glucuronidase (GUS) reporter gene.

34. The vector of claim 33, wherein said GUS reporter gene is derived from the vector pBI101, pBI121, pBI221 or pCTGus.

35. A DNA fusion comprising a DNA segment encoding an exogenous protein, other than the product of the PAT1 gene, operatively linked to exons 1 and 2, 8 codons of exon 3, and intron 1 or intron 2 of the PAT1 gene.

36. The DNA fusion of claim 35, comprising a DNA segment encoding an exogenous protein operatively linked to exons 1 and 2, 8 codons of exon 3, and intron 1 of the PAT1 gene.

37. The DNA fusion of claim 35, comprising a DNA segment encoding an exogenous protein operatively linked to exons 1 and 2, 8 codons of exon 3, and intron 2 of the PAT1 gene.

38. The DNA fusion of claim 35 comprising a DNA segment encoding an exogenous protein operatively linked to exons 1 and 2, 8 codons of exon 3 and introns 1 and 2 of the PAT1 gene.

39. The DNA fusion of claim 35, wherein said DNA segment encodes a reporter gene.

40. The DNA fusion of claim 39, wherein said DNA segment is furter defined as encoding β-glucuronidase (GUS) reporter gene.

41. The DNA fusion of claim 40, wherein said GUS reporter gene is derived from pBI101, pBI121, pBI221, or pCTGus.

42. The DNA fusion of claim 35, wherein said DNA segment encodes a protein of pharmacological interest.

43. The DNA fusion of claim 42, wherein said DNA segment encodes an animal vaccine gene in accordance with Table 2.

44. The DNA fision of claim 42, wherein said DNA segment encodes a human vaccine gene in accordance with Table 2.

45. The DNA fusion of claim 44, wherein said DNA segment encodes Hepatitis B surface antigen.

46. A DNA fusion comprising a DNA segment encoding an exogenous protein, other than the product of the PAT1 gene, operatively linked to exon 3 and intron 2 of the PAT1.

47. A DNA fusion consisting essentially of at least one intron and a DNA segment encoding the entire chloroplast transit peptide of the PAT1 gene.

48. The DNA fusion of claim 47, wherein said DNA segment encoding chloroplast transit peptide of PAT1 is further defined as comprising exon 1 and at least 10 codons of exon 2 of the PAT1 gene.

49. A DNA fusion consisting essentially of at least one intron and a DNA segment comprising at least 60 codons of the chloroplast transit peptide of the PAT1 gene.

50. An isolated polynucleotide of the PAT1 gene consisting essentially of exon 1, 2 or 3 and intron 1 or intron 2 of the PAT1 gene.

51. The polynucleotide of claim 50, wherein said polynucleotide comprises intron 1 of the PAT1 gene.

52. The polynucleotide of claim 51, wherein said polynucleotide further comprises exon 1 of the PAT1 gene.

53. The polynucleotide of claim 50, wherein said polynucleotide comprises intron 2 of the PAT1 gene.

54. The polynucleotide of claim 53, wherein said polynucleotide farther comprises exon 3 of the PAT1 gene.

55. The polynucleotide of claim 50, wherein said polynucleotide comprises intron 1 and intron 2 of the PAT1 gene.

56. The polynucleotide of claim 55, wherein said polynucleotide further comprises exon 3 of the PAT1 gene.

57. An expression vector comprising a polynucleotide in accordance with any one of claims 51–56.

58. A cell transformed with the expression vector of claim 57.

59. The cell of claim 58, wherein said cell is further defined as a plant cell.

60. The cell of claim 59, wherein said cell is further defined as a wild-type Arabidopsis cell.

61. A construct that increases the expression of exogenous protein RNA in transgenic plants, said construct comprising exons 1 and 2, introns 1 and 2, and 8 codons of exon 3 of the PAT1 gene operatively linked to a DNA segment encoding the exogenous protein one desires to express, wherein the exogenous protein is a protein other than the PAT1 gene product.

62. A plant cell transformed with a DNA fusion in accordance with any one of claims 21–35, wherein said cell comprises an increased number of exogenous protein RNAs in comparison to a plant cell not transformed with said transgene, wherein the exogenous protein RNA is not PAT1 RNA.

63. A recombinant host cell comprising an exogenous fusion protein, wherein said fusion comprises a DNA fusion in accordance with any one of claims 35–49.

64. The recombinant host cell of claim 63, wherein said exogenous fusion protein is introduced into said cell by means of a recombinant vector.

65. A recombinant host cell comprising a DNA fusion in accordance with any one of claims 35–49.

66. The recombinant host cell of claim 65, wherein said DNA fusion is introduced into said cell by means of a recombinant vector.

67. A method of expression comprising fusing a portion of the PAT1 gene operatively linked with a DNA segment encoding an exogenous protein one desires to express, wherein said DNA segment does not encode the PAT1 gene product, and introducing said fusion into wild-type Arabidopsis.

68. The method of claim 67, wherein said fusion comprises exon 1 and exon 2, 8 codons of exon 3 and intron 1 or intron 2 of the PAT1 gene.

69. The method of claim 68, wherein said fusion comprises exon 1, intron 1, exon 2, and 8 codons of exon 3 of the PAT1 gene.

70. The method of claim 68, wherein said fusion comprises exon 1, exon 2, intron 2, and 8 codons of exon 3 of the PAT1 gene.

71. The method of claim 68, wherein said fusion comprises exon 1, intron 1, exon 2 intron 2 and 8 codons of exon 3 of the PAT1 gene.

72. The method of claim 67, wherein said fusion is introduced into said Arabidopsis by means of *Agrobacterium tumefaciens*-mediated vacuum filtration method.

73. The method of claim 67, wherein said fusion is introduced into said Arabidopsis by means of the root explant method.

74. A transformed plant line comprising a DNA fusion in accordance with any one of claims 35–49, wherein said line contains single and unique site of transgene insertion.

75. A transformed plant line comprising a transgene encoding the entire chloroplast transit peptide of PAT1, operatively linked to a transgene, other than the PAT1 gene.

76. The plant line of claim 75, farther comprising intron 1 of the PAT1 gene.

77. The plant line of claim 76, wherein said transgene encoding transit peptide is further defined as having the nucleotide sequence of SEQ ID NO:1.

78. The plant line of claim 76 prepared by the process of creating a translational fusion protein gene and introducing said fusion into a plant.

79. The plant line of claim 78, wherein said plant is further defined as a wild-type Arabidopsis.

80. The plant line of claim 78, wherein said plant is further defined as a food plant.

81. The plant line of claim 80, wherein said plant is further defined as a tobacco plant, potato plant, a banana plant, a tomato plant, or any member of the plant genus Brassica.

82. The plant line of claim 81, wherein said plant is further defined as a potato plant.

83. A transformed plant line comprising a transgene comprising an exogenous protein gene, other than the PAT1 gene, operatively linked to exons 1 and 2, intron 1 or intron 2 and 8 codons of exon 3 of the PAT1 gene.

84. The plant line of claim 83, prepared by the process of creating a translational fusion protein gene and introducing said fusion into a plant.

85. The plant line of claim 83, wherein said fusion is further defined as comprising intron 1 of the PAT1 gene.

86. The plant line of claim 83, wherein said fusion is further defined as comprising intron 2 of the PAT1 gene.

87. The plant line of claim 83, wherein said fusion is further defined as comprising intron 1 and intron 2 of the PAT1 gene.

88. A cultivated, transgenic food plant, the genome of which has been augmented through the genomic introduction of a preselected exogenous protein gene not found in the genome of non-transformed parentage of said plant, the plant preparable by a process that includes the steps of:

a) preparing a nucleic acid composition including the exogenous protein gene one desires to introduce into the genome of a food plant, said gene operatively linked to at least one intron of the PAT1 gene;

b) contacting recipient food cells with said composition under conditions allowing the uptake of the exogenous protein gene by recipient cells;

c) regenerating food plants from recipient cells which have received the exogenous protein gene; and d) identifying a fertile, transgenic food plant whose genome has been augmented relative to that of the corresponding nontransgenic recipient cells through the stable introduction of said exogenous protein gene, wherein said exogenous protein is not the PAT1 gene.

89. Progeny of the plant of claim 88.

90. Seed obtained from the plant of claim 88.

91. Cells obtained from the plant of claim 88.

* * * * *

UNITED STATES PATENT AND TRADEMARK OFFICE
CERTIFICATE OF CORRECTION

PATENT NO. : 5,861,277
DATED : January 19, 1999
INVENTOR(S) : Rose et al.

It is certified that error appears in the above-identified patent and that said Letters Patent is hereby corrected as shown below:

In claim 62, column 52, line 17, delete "21-35", and insert the following therefor: -- 35-49 --.

In claim 76, column 52, line 63, delete "farther", and insert the following therefor: -- further --.

Signed and Sealed this

Thirteenth Day of July, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 249 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ATGGTTATTG  CGGTGGCGAC  GACGAGCTCC  ATTGTTTCCG  GAATCAAGCT  TTCAGGGATC         60

TTAACTTCGT  TCAACGCCGT  AGATGATGCG  TCCAGTAGTT  GCGGAAGAAG  CAACTTGACC        120

GGAGTTAGAA  TTTTTCCGAC  ATTGAGTCGG  CGACGATTCT  CATCGATCGG  AGCTGTTTCC        180

CCAATTCGTG  GGGATGCTCA  ATCTTCCTTT  AGTCGCAGCT  CTTTCGCTTG  CTCTCAGAAT        240

CTCGGTTTG                                                                    249
```

( 2 ) INFORMATION FOR SEQ ID NO:2:

( i ) SEQUENCE CHARACTERISTICS:
        ( A ) LENGTH: 180 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
ATGGTTATTG  CGGTGGCGAC  GACGAGCTCC  ATTGTTTCCG  GAATCAAGCT  TTCAGGGATC         60

TTAACTTCGT  TCAACGCCGT  AGATGATGCG  TCCAGTAGTT  GCGGAAGAAG  CAACTTGACC        120

GGAGTTAGAA  TTTTTCCGAC  ATTGAGTCGG  CGACGATTCT  CATCGATCGG  AGCTGTTTCC        180
```

( 2 ) INFORMATION FOR SEQ ID NO:3:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GTAAAGCCTC  GATTTTTGGG  TTTAGGTGTC  TGCTTATTAG  AGTAAAAACA  CATCCTTTGA         60

AATTGTTTGT  GGTCATTTGA  TTGTGCTCTT  GATCCATTGA  ATTGCTGCAG                    110
```

( 2 ) INFORMATION FOR SEQ ID NO:4:

( i ) SEQUENCE CHARACTERISTICS:
        ( A ) LENGTH: 116 base pairs ( B ) TYPE: nucleic acid
( C ) STRANDEDNESS: single
( D ) TOPOLOGY: linear ( x i ) SEQUENCE DESCRIPTION: SEQ ID NO:4:

| | | | | | |
|---|---|---|---|---|---|
| CTGCAGGTAA | AGCCTCGATT | TTTGGGTTTA | GGTGTCTGCT | TATTAGAGTA | AAAACACATC | 60 |
| CTTTGAAATT | GTTTGTGGTC | ATTTGATTGT | GCTCTTGATC | CATTGAATTG | CTGCAG | 116 |

( 2 ) INFORMATION FOR SEQ ID NO:5:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| | | | | | |
|---|---|---|---|---|---|
| CTGCAGGTAA | AGTCTTGATT | TTGGGTTTAG | GTGTCTGCTT | ATTAGAGTAA | AAACACATTC | 60 |
| TTTGACGTCT | TTTGTGGTCA | TTTGATTTGA | ATCTAGGAAT | CTAATTGTGC | TCTTGATCCA | 120 |
| TTGAATTGCT | GCAG | | | | | 134 |

( 2 ) INFORMATION FOR SEQ ID NO:6:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| | | | | | |
|---|---|---|---|---|---|
| CTGCAGGTAA | AGTCTTGATT | TTTGGGTTTA | GGTGTCTGCT | TATTAGAGTA | AAAACACATC | 60 |
| CTTTGAAATT | GTTTGTGGTC | ATTTGATTGT | GCTCTTGATC | CATTGAATTG | CTGCAG | 116 |

( 2 ) INFORMATION FOR SEQ ID NO:7:

( i ) SEQUENCE CHARACTERISTICS:
        ( A ) LENGTH: 352 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | | | |
|---|---|---|---|---|---|
| GTGACTCTTC | ATTTCTATTT | TCAGGATAAG | TTTGTGGTTT | GATGATCCCT | TGTTTCTAAG | 60 |
| TCTCTTGATT | TGTGAACAAT | TCAGGGTTTT | TATATATCTG | TATCTGTATT | TCTGAGTTGG | 120 |
| GTTGAGTTAT | TGGCTTCATG | CTGACTAAAC | ATGTTTGGCC | CTGTGTGTTC | TTCGAATTTC | 180 |
| ATTTTAATTG | CTTGATGGGT | TTTATTGACT | TGAGTAAAAG | TGTACTACTT | TATAGGTTTT | 240 |
| AAAAGAGTTT | TACTTTTGGT | GATTTTCCAA | TGGCTTTGAA | GAGAGAGATT | TAAATCATGG | 300 |
| GGTTACTATG | TTCTCATACT | GCGTTTGCTC | TGTTCTGTTG | TTTTTCTTTC | AG | 352 |

( 2 ) INFORMATION FOR SEQ ID NO:8:

( i ) SEQUENCE CHARACTERISTICS:
        ( A ) LENGTH: 218 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

| | | | | | |
|---|---|---|---|---|---|
| ATGGTTATTG | CGGTGGCGAC | GACGAGCTCC | ATTGTTTCCG | GAATCAAGCT | TTCAGGGATC | 60 |
| TTAACTTCGT | TCAACGCCGT | AGATGATGCG | TCCAGTAGTT | GCGGAAGAAG | CAACTTGACC | 120 |

(2) INFORMATION FOR SEQ ID NO:9:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (xi) SEQUENCE DESCRIPTION: SEQ ID NO:9:

```
CTCTTTCGCT TGCTCTCAGA ATCTCGGTTT GAGCGGTGGA TTTAGTGCAG CTGAAGCTCT      60
GCCACCTGCT TGTGCAAATG CTAGCCCTTC TTCCATTAAA TCTTTCAACC AG             112
```

(2) INFORMATION FOR SEQ ID NO:10:

(i) SEQUENCE CHARACTERISTICS:
        (A) LENGTH: 144 base pairs
        (B) TYPE: nucleic acid
        (C) STRANDEDNESS: single
        (D) TOPOLOGY: linear (xi) SEQUENCE DESCRIPTION: SEQ ID NO:10:

```
TTGATTGAAA CCTTGATTGA TCGGGTTGAT CTATCTGAAA CTGAGGCTGA ATCATCTCTT      60
GAGTTTTTGC TGAATGAGGC AAACGAGGCG CTGATCAGTG CCTTTCTAGT TCTTCTGAGA     120
GCTAAAGGAG AGACATACGA AGAG                                           144
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:11:

```
TTGATTGAAA CCTTGATTGA TCGGTCTAGA                                      30
```

(2) INFORMATION FOR SEQ ID NO:12:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (xi) SEQUENCE DESCRIPTION: SEQ ID NO:12:

```
ATGGTTATTG CGGTGGCGAC GACGAGCTCC ATTGTTTCCG GAATCAAGCT TTCAGGGATC      60
TTAACTTCGT TCAACGCCGT AGATGATGCG TCCAGTAGTT GCGGAAGAAG CAACTTGACC     120
GGAGTTAGAA TTTTTCCGAC ATTGAGTCGG CGACGATTCT CATCGATCGG AGCTGTTTCC     180
CCAATTCGTG GGGATGCTCA ATCTTCCTTT AGTCGCAGGT AAAGCCTCGA TTTTGGGTT      240
TAGGTGTCTG CTTATTAGAG TAAAAACACA TCCTTTGAAA TTGTTTGTGG TCATTTGATT     300
GTGCTCTTGA TCCATTGAAT TGCTGCAGCT CTTTCGCTTG CTCTCAGAAT CTCGGTTTGA     360
GCGGTGGATT TAGTGCAGCT GAAGCTCTGC CACCTGCTTG TGCAAATGCT AGCCCTTCTT     420
CCATTAAATC TTTCAACCAG TTGATTGAAA CCTTGATTGA TCGGTCTAGA                470
```

(2) INFORMATION FOR SEQ ID NO:13:

(i) SEQUENCE CHARACTERISTICS:

(A) LENGTH: 712 base pairs
(B) TYPE: nucleic acid
(C) STRANDEDNESS: single
(D) TOPOLOGY: linear (xi) SEQUENCE DESCRIPTION: SEQ ID NO:13:

| | | | | | | |
|---|---|---|---|---|---|---|
| ATGGTTATTG | CGGTGGCGAC | GACGAGCTCC | ATTGTTTCCG | GAATCAAGCT | TTCAGGGATC | 60 |
| TTAACTTCGT | TCAACGCCGT | AGATGATGCG | TCCAGTAGTT | GCGGAAGAAG | CAACTTGACC | 120 |
| GGAGTTAGAA | TTTTTCCGAC | ATTGAGTCGG | CGACGATTCT | CATCGATCGG | AGCTGTTTCC | 180 |
| CCAATTCGTG | GGGATGCTCA | ATCTTCCTTT | AGTCGCAGCT | CTTTCGCTTG | CTCTCAGAAT | 240 |
| CTCGGTTTGA | GCGGTGGATT | TAGTGCAGCT | GAAGCTCTGC | CACCTGCTTG | TGCAAATGCT | 300 |
| AGCCCTTCTT | CCATTAAATC | TTTCAACCAG | GTGACTCTTC | ATTTCTATTT | TCAGGATAAG | 360 |
| TTTGTGGTTT | GATGATCCCT | TGTTTCTAAG | TCTCTTGATT | TGTGAACAAT | TCAGGGTTTT | 420 |
| TATATATCTG | TATCTGTATT | TCTGAGTTGG | GTTGAGTTAT | TGGCTTCATG | CTGACTAAAC | 480 |
| ATGTTTGGCC | CTGTGTGTTC | TTCGAATTTC | ATTTAATTG | CTTGATGGGT | TTTATTGACT | 540 |
| TGAGTAAAAG | TGTACTACTT | TATAGGTTTT | AAAAGAGTTT | TACTTTGGT | GATTTTCCAA | 600 |
| TGGCTTTGAA | GAGAGAGATT | TAAATCATGG | GGTTACTATG | TTCTCATACT | GCGTTTGCTC | 660 |
| TGTTCTGTTG | TTTTTCTTTC | AGTTGATTGA | AACCTTGATT | GATCGGTCTA | GA | 712 |

(2) INFORMATION FOR SEQ ID NO:14:

(i) SEQUENCE CHARACTERISTICS:
(A) LENGTH: 822 base pairs
(B) TYPE: nucleic acid
(C) STRANDEDNESS: single
(D) TOPOLOGY: linear (xi) SEQUENCE DESCRIPTION: SEQ ID NO:14:

| | | | | | | |
|---|---|---|---|---|---|---|
| ATGGTTATTG | CGGTGGCGAC | GACGAGCTCC | ATTGTTTCCG | GAATCAAGCT | TTCAGGGATC | 60 |
| TTAACTTCGT | TCAACGCCGT | AGATGATGCG | TCCAGTAGTT | GCGGAAGAAG | CAACTTGACC | 120 |
| GGAGTTAGAA | TTTTTCCGAC | ATTGAGTCGG | CGACGATTCT | CATCGATCGG | AGCTGTTTCC | 180 |
| CCAATTCGTG | GGGATGCTCA | ATCTTCCTTT | AGTCGCAGGT | AAAGCCTCGA | TTTTTGGGTT | 240 |
| TAGGTGTCTG | CTTATTAGAG | TAAAAACACA | TCCTTTGAAA | TTGTTTGTGG | TCATTTGATT | 300 |
| GTGCTCTTGA | TCCATTGAAT | TGCTGCAGCT | CTTTCGCTTG | CTCTCAGAAT | CTCGGTTTGA | 360 |
| GCGGTGGATT | TAGTGCAGCT | GAAGCTCTGC | CACCTGCTTG | TGCAAATGCT | AGCCCTTCTT | 420 |
| CCATTAAATC | TTTCAACCAG | GTGACTCTTC | ATTTCTATTT | TCAGGATAAG | TTTGTGGTTT | 480 |
| GATGATCCCT | TGTTTCTAAG | TCTCTTGATT | TGTGAACAAT | TCAGGGTTTT | TATATATCTG | 540 |
| TATCTGTATT | TCTGAGTTGG | GTTGAGTTAT | TGGCTTCATG | CTGACTAAAC | ATGTTTGGCC | 600 |
| CTGTGTGTTC | TTCGAATTTC | ATTTAATTG | CTTGATGGGT | TTTATTGACT | TGAGTAAAAG | 660 |
| TGTACTACTT | TATAGGTTTT | AAAAGAGTTT | TACTTTGGT | GATTTTCCAA | TGGCTTTGAA | 720 |
| GAGAGAGATT | TAAATCATGG | GGTTACTATG | TTCTCATACT | GCGTTTGCTC | TGTTCTGTTG | 780 |
| TTTTTCTTTC | AGTTGATTGA | AACCTTGATT | GATCGGTCTA | GA | | 822 |

(2) INFORMATION FOR SEQ ID NO:15:

(i) SEQUENCE CHARACTERISTICS:
(A) LENGTH: 359 base pairs
(B) TYPE: nucleic acid
(C) STRANDEDNESS: single
(D) TOPOLOGY: linear (xi) SEQUENCE DESCRIPTION: SEQ ID NO:15:

```
ATGGTTATTG  CGGTGGCGAC  GACGAGCTCC  ATTGTTTCCG  GAATCAAGCT  TTCAGGGATC     60

TTAACTTCGT  TCAACGCCGT  AGATGATGCG  TCCAGTAGTT  GCGGAAGAAG  CAACTTGACC    120

GGAGTTAGAA  TTTTCCGAC   ATTGAGTCGG  CGACGATTCT  CATCGATCGG  AGCTGTTTCC    180

CCAATTCGTG  GGGATGCTCA  ATCTTCCTTT  AGTCGCAGGT  AAAGCCTCGA  TTTTGGGTT    240

TAGGTGTCTG  CTTATTAGAG  TAAAAACACA  TCCTTTGAAA  TTGTTTGTGG  TCATTTGATT   300

GTGCTCTTGA  TCCATTGAAT  TGCTGCAGCT  CTTTCGCTTG  CTCTCAGAAT  CTCGGTTTG    359
```

( 2 ) INFORMATION FOR SEQ ID NO:16:

( i ) SEQUENCE CHARACTERISTICS:
           ( A ) LENGTH: 24 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:16:

```
GATAATCTAG  AGCTCGTCGT  CGCC                                               24
```

( 2 ) INFORMATION FOR SEQ ID NO:17:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:17:

```
GTTGCTCTAG  ACCGATCAAT  CAAGG                                              25
```

( 2 ) INFORMATION FOR SEQ ID NO:18:

( i ) SEQUENCE CHARACTERISTICS:
           ( A ) LENGTH: 3035 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:18:

```
GTCGACGTGG  TGCGGTGGGT  TGATGACACC  CGTTTCTGGA  AGAATCCGAC  ATCAACTTTA     60

CTAGTTCACG  CACTTGTCGT  GATGCTGATT  TGGTTCCCGG  ATCTTATCGT  ACCGACATTA    120

GCGTTTTACT  TGTTCGTGAT  TGGTGCGTGG  AATTATAGGT  TCAGGTCACG  TGCTGCTCTA    180

CCACATTTCG  ATCCAAGACT  CTCGTTAGCT  GATGCAGCTG  ATAGAGACGA  GCTCGACGAG    240

GAGTTTGACG  TCGTACCGAG  CAACCGACCA  CCGGAGATGG  TTCGGTTGAG  GTACGATAAG    300

CTACGAAACG  TCGGAGCTAG  AGTTCAAACG  ATTCTTGGTG  AAGTGGCTGC  GCAAGGGGAG    360

AAGATGCAAG  CTTTGGTGAC  GTGGCGTGAC  CCACGAGCGA  CTGGTATATT  CGTGGGGCTG    420

TGTTTCTTTG  TGGCGTTGGT  GTTGTATCTT  GTGCCGACGA  AGATGGTGGC  TATGGCGTCA    480

GGGTTTTATT  ACTTCCGGCA  TCCTATTTTC  CGTGATCGGA  AACCTTCTCC  GGTGTTAAAT    540

TTCTTCCGGC  GACTACCATC  ATTATCTGAT  CGGCTCATGT  AATATTGTTT  TTTTTTTTGG    600

AGGGGATGTA  TATATAGTTT  GGGTCGTTTA  ACCTTGTTGG  GCCTTATTGG  GTTATAATGG    660

GCCACTAAAT  GGATTTTTAT  ATGATTTCCT  ATTATAGGTG  CTGTGTTTGA  CCATGTCTAA    720

AACAAAGAAG  TGTTTGGTAT  GACAAAATTG  ATGAACCTAC  TTTTTGAGCA  GAGTGGTAAA    780

TGTGCGGAAA  TAAGCACACA  AGGAAATCGT  TGTTGGTGAC  TAACAAAAGG  AGTTATCCAC    840

TGCCCAAGCA  TTACCAACTA  CCACCAACCA  AACTCAATTT  GGAAATTTCA  AAGGTCCATT    900
```

| | | | | | | |
|---|---|---|---|---|---|---|
| AGTCAAAGCA | GCATTAAGTC | ATTCAGTAAT | CAACAAATAT | ATTCATATGA | AACCCAAAAT | 960 |
| AAAATAAAAT | AAACACTTTT | CAAGAAAAAA | ATAAATACT | GAGTACTAAA | CTGGAAACCC | 1020 |
| TTTATAAGCA | AAAAGACCAA | AAGTTAAAAG | TTAATTAAGA | TTTGGTTTAA | GGCGCTTTGC | 1080 |
| TTTATTAGAG | AGGAAGGAAC | GAACCATCAT | AGAAATCTCT | CCTTCGTTCA | AGTTTTTCTC | 1140 |
| TACTGTGTTG | GTTGAGCAAT | CGAGTGATGG | TTATTGCGGT | GGCGACGACG | AGCTCTAGAG | 1200 |
| GATCCCCGGG | TGGTCAGTCC | CTTCTGTTAC | GTCCTGTAGA | AACCCCAACC | CGTGAAATCA | 1260 |
| AAAAACTCGA | CGGCCTGTGG | GCATTCAGTC | TGGATCGCGA | AAACTGTGGA | ATTGATCAGC | 1320 |
| GTTGGTGGGA | AAGCGCGTTA | CAAGAAAGCC | GGGCAATTGC | TGTGCCAGGC | AGTTTTAACG | 1380 |
| ATCAGTTCGC | CGATGCAGAT | ATTCGTAATT | ATGCGGGCAA | CGTCTGGTAT | CAGCGCGAAG | 1440 |
| TCTTTATACC | GAAAGGTTGG | GCAGGCCAGC | GTATCGTGCT | GCGTTTCGAT | GCGGTCACTC | 1500 |
| ATTACGGCAA | AGTGTGGGTC | AATAATCAGG | AAGTGATGGA | GCATCAGGGC | GGCTATACGC | 1560 |
| CATTTGAAGC | CGATGTCACG | CCGTATGTTA | TTGCCGGGAA | AAGTGTACGT | ATCACCGTTT | 1620 |
| GTGTGAACAA | CGAACTGAAC | TGGCAGACTA | TCCCGCCGGG | AATGGTGATT | ACCGACGAAA | 1680 |
| ACGGCAAGAA | AAAGCAGTCT | TACTTCCATG | ATTTCTTTAA | CTATGCCGGA | ATCCATCGCA | 1740 |
| GCGTAATGCT | CTACACCACG | CCGAACACCT | GGGTGGACGA | TATCACCGTG | GTGACGCATG | 1800 |
| TCGCGCAAGA | CTGTAACCAC | GCGTCTGTTG | ACTGGCAGGT | GGTGGCCAAT | GGTGATGTCA | 1860 |
| GCGTTGAACT | GCGTGATGCG | GATCAACAGG | TGGTTGCAAC | TGGACAAGGC | ACTAGCGGGA | 1920 |
| CTTTGCAAGT | GGTGAATCCG | CACCTCTGGC | AACCGGGTGA | AGGTTATCTC | TATGAACTGT | 1980 |
| GCGTCACAGC | CAAAAGCCAG | ACAGAGTGTG | ATATCTACCC | GCTTCGCGTC | GGCATCCGGT | 2040 |
| CAGTGGCAGT | GAAGGGCGAA | CAGTTCCTGA | TTAACCACAA | ACCGTTCTAC | TTTACTGGCT | 2100 |
| TTGGTCGTCA | TGAAGATGCG | GACTTGCGTG | GCAAAGGATT | CGATAACGTG | CTGATGGTGC | 2160 |
| ACGACCACGC | ATTAATGGAC | TGGATTGGGG | CCAACTCCTA | CCGTACCTCG | CATTACCCTT | 2220 |
| ACGCTGAAGA | GATGCTCGAC | TGGGCAGATG | AACATGGCAT | CGTGGTGATT | GATGAAACTG | 2280 |
| CTGCTGTCGG | CTTTAACCTC | TCTTTAGGCA | TTGGTTTCGA | AGCGGGCAAC | AAGCCGAAAG | 2340 |
| AACTGTACAG | CGAAGAGGCA | GTCAACGGGG | AAACTCAGCA | AGCGCACTTA | CAGGCGATTA | 2400 |
| AAGAGCTGAT | AGCGCGTGAC | AAAAACCACC | CAAGCGTGGT | GATGTGGAGT | ATTGCCAACG | 2460 |
| AACCGGATAC | CCGTCCGCAA | GGTGCACGGG | AATATTTCGC | GCCACTGGCG | GAAGCAACGC | 2520 |
| GTAAACTCGA | CCCGACGCGT | CCGATCACCT | GCGTCAATGT | AATGTTCTGC | GACGCTCACA | 2580 |
| CCGATACCAT | CAGCGATCTC | TTTGATGTGC | TGTGCCTGAA | CCGTTATTAC | GGATGGTATG | 2640 |
| TCCAAAGCGG | CGATTTGGAA | ACGGCAGAGA | AGGTACTGGA | AAAAGAACTT | CTGGCCTGGC | 2700 |
| AGGAGAAACT | GCATCAGCCG | ATTATCATCA | CCGAATACGG | CGTGGATACG | TTAGCCGGGC | 2760 |
| TGCACTCAAT | GTACACCGAC | ATGTGGAGTG | AAGAGTATCA | GTGTGCATGG | CTGGATATGT | 2820 |
| ATCACCGCGT | CTTTGATCGC | GTCAGCGCCG | TCGTCGGTGA | ACAGGTATGG | AATTTCGCCG | 2880 |
| ATTTTGCGAC | CTCGCAAGGC | ATATTGCGCG | TTGGCGGTAA | CAAGAAAGGG | ATCTTCACTC | 2940 |
| GCGACCGCAA | ACCGAAGTCG | GCGGCTTTTC | TGCTGCAAAA | ACGCTGGACT | GGCATGAACT | 3000 |
| TCGGTGAAAA | ACCGCAGCAG | GGAGGCAAAC | AATGA | | | 3035 |

( 2 ) INFORMATION FOR SEQ ID NO:19:

( i ) SEQUENCE CHARACTERISTICS:
        ( A ) LENGTH: 3824 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

| | | | | | |
|---|---|---|---|---|---|
| GTCGACGTGG | TGCGGTGGGT | TGATGACACC | CGTTTCTGGA | AGAATCCGAC | ATCAACTTTA | 60
| CTAGTTCACG | CACTTGTCGT | GATGCTGATT | TGGTTCCCGG | ATCTTATCGT | ACCGACATTA | 120
| GCGTTTTACT | TGTTCGTGAT | TGGTGCGTGG | AATTATAGGT | TCAGGTCACG | TGCTGCTCTA | 180
| CCACATTTCG | ATCCAAGACT | CTCGTTAGCT | GATGCAGCTG | ATAGAGACGA | GCTCGACGAG | 240
| GAGTTTGACG | TCGTACCGAG | CAACCGACCA | CCGGAGATGG | TTCGGTTGAG | GTACGATAAG | 300
| CTACGAAACG | TCGGAGCTAG | AGTTCAAACG | ATTCTTGGTG | AAGTGGCTGC | GCAAGGGGAG | 360
| AAGATGCAAG | CTTTGGTGAC | GTGGCGTGAC | CCACGAGCGA | CTGGTATATT | CGTGGGGCTG | 420
| TGTTTCTTTG | TGGCGTTGGT | GTTGTATCTT | GTGCCGACGA | AGATGGTGGC | TATGGCGTCA | 480
| GGGTTTTATT | ACTTCCGGCA | TCCTATTTTC | CGTGATCGGA | AACCTTCTCC | GGTGTTAAAT | 540
| TTCTTCCGGC | GACTACCATC | ATTATCTGAT | CGGCTCATGT | AATATTGTTT | TTTTTTTTGG | 600
| AGGGGATGTA | TATATAGTTT | GGGTCGTTTA | ACCTTGTTGG | GCCTTATTGG | GTTATAATGG | 660
| GCCACTAAAT | GGATTTTTAT | ATGATTTCCT | ATTATAGGTG | CTGTGTTTGA | CCATGTCTAA | 720
| AACAAAGAAG | TGTTTGGTAT | GACAAAATTG | ATGAACCTAC | TTTTTGAGCA | GAGTGGTAAA | 780
| TGTGCGGAAA | TAAGCACACA | AGGAAATCGT | TGTTGGTGAC | TAACAAAAGG | AGTTATCCAC | 840
| TGCCCAAGCA | TTACCAACTA | CCACCAACCA | AACTCAATTT | GGAAATTTCA | AAGGTCCATT | 900
| AGTCAAAGCA | GCATTAAGTC | ATTCAGTAAT | CAACAAATAT | ATTCATATGA | AACCCAAAAT | 960
| AAAATAAAAT | AAACACTTTT | CAAGAAAAAA | ATAAAATACT | GAGTACTAAA | CTGGAAACCC | 1020
| TTTATAAGCA | AAAAGACCAA | AAGTTAAAAG | TTAATTAAGA | TTTGGTTTAA | GGCGCTTTGC | 1080
| TTTATTAGAG | AGGAAGGAAC | GAACCATCAT | AGAAATCTCT | CCTTCGTTCA | AGTTTTCTC | 1140
| TACTGTGTTG | GTTGAGCAAT | CGAGTGATGG | TTATTGCGGT | GGCGACGACG | AGCTCCATTG | 1200
| TTTCCGGAAT | CAAGCTTTCA | GGGATCTTAA | CTTCGTTCAA | CGCCGTAGAT | GATGCGTCCA | 1260
| GTAGTTGCGG | AAGAAGCAAC | TTGACCGGAG | TTAGAATTTT | TCCGACATTG | AGTCGGCGAC | 1320
| GATTCTCATC | GATCGGAGCT | GTTTCCCCAA | TTCGTGGGGA | TGCTCAATCT | TCCTTTAGTC | 1380
| GCAGGTAAAG | CCTCGATTTT | TGGGTTTAGG | TGTCTGCTTA | TTAGAGTAAA | AACACATCCT | 1440
| TTGAAATTGT | TTGTGGTCAT | TTGATTGTGC | TCTTGATCCA | TTGAATTGCT | GCAGCTCTTT | 1500
| CGCTTGCTCT | CAGAATCTCG | GTTTGAGCGG | TGGATTTAGT | GCAGCTGAAG | CTCTGCCACC | 1560
| TGCTTGTGCA | AATGCTAGCC | CTTCTTCCAT | TAAATCTTTC | AACCAGGTGA | CTCTTCATTT | 1620
| CTATTTTCAG | GATAAGTTTG | TGGTTTGATG | ATCCCTTGTT | TCTAAGTCTC | TTGATTTGTG | 1680
| AACAATTCAG | GGTTTTTATA | TATCTGTATC | TGTATTTCTG | AGTTGGGTTG | AGTTATTGGC | 1740
| TTCATGCTGA | CTAAACATGT | TTGGCCCTGT | GTGTTCTTCG | AATTTCATTT | TAATTGCTTG | 1800
| ATGGGTTTTA | TTGACTTGAG | TAAAAGTGTA | CTACTTTATA | GGTTTTAAAA | GAGTTTTACT | 1860
| TTTGGTGATT | TTCCAATGGC | TTTGAAGAGA | GAGATTTAAA | TCATGGGGTT | ACTATGTTCT | 1920
| CATACTGCGT | TTGCTCTGTT | CTGTTGTTTT | TCTTTCAGTT | GATTGAAACC | TTGATTGATC | 1980
| GGTCTAGAGG | ATCCCCGGGT | GGTCAGTCCC | TTCTGTTACG | TCCTGTAGAA | ACCCCAACCC | 2040
| GTGAAATCAA | AAAACTCGAC | GGCCTGTGGG | CATTCAGTCT | GGATCGCGAA | AACTGTGGAA | 2100
| TTGATCAGCG | TTGGTGGGAA | AGCGCGTTAC | AAGAAAGCCG | GGCAATTGCT | GTGCCAGGCA | 2160
| GTTTTAACGA | TCAGTTCGCC | GATGCAGATA | TTCGTAATTA | TGCGGGCAAC | GTCTGGTATC | 2220
| AGCGCGAAGT | CTTTATACCG | AAAGGTTGGG | CAGGCCAGCG | TATCGTGCTG | CGTTTCGATG | 2280
| CGGTCACTCA | TTACGGCAAA | GTGTGGGTCA | ATAATCAGGA | AGTGATGGAG | CATCAGGGCG | 2340

```
GCTATACGCC  ATTTGAAGCC  GATGTCACGC  CGTATGTTAT  TGCCGGGAAA  AGTGTACGTA      2400

TCACCGTTTG  TGTGAACAAC  GAACTGAACT  GGCAGACTAT  CCCGCCGGGA  ATGGTGATTA      2460

CCGACGAAAA  CGGCAAGAAA  AAGCAGTCTT  ACTTCCATGA  TTTCTTTAAC  TATGCCGGAA      2520

TCCATCGCAG  CGTAATGCTC  TACACCACGC  CGAACACCTG  GGTGGACGAT  ATCACCGTGG      2580

TGACGCATGT  CGCGCAAGAC  TGTAACCACG  CGTCTGTTGA  CTGGCAGGTG  GTGGCCAATG      2640

GTGATGTCAG  CGTTGAACTG  CGTGATGCGG  ATCAACAGGT  GGTTGCAACT  GGACAAGGCA      2700

CTAGCGGGAC  TTTGCAAGTG  GTGAATCCGC  ACCTCTGGCA  ACCGGGTGAA  GGTTATCTCT      2760

ATGAACTGTG  CGTCACAGCC  AAAAGCCAGA  CAGAGTGTGA  TATCTACCCG  CTTCGCGTCG      2820

GCATCCGGTC  AGTGGCAGTG  AAGGGCGAAC  AGTTCCTGAT  TAACCACAAA  CCGTTCTACT      2880

TTACTGGCTT  TGGTCGTCAT  GAAGATGCGG  ACTTGCGTGG  CAAAGGATTC  GATAACGTGC      2940

TGATGGTGCA  CGACCACGCA  TTAATGGACT  GGATTGGGGC  CAACTCCTAC  CGTACCTCGC      3000

ATTACCCTTA  CGCTGAAGAG  ATGCTCGACT  GGGCAGATGA  ACATGGCATC  GTGGTGATTG      3060

ATGAAACTGC  TGCTGTCGGC  TTTAACCTCT  CTTTAGGCAT  TGGTTTCGAA  GCGGGCAACA      3120

AGCCGAAAGA  ACTGTACAGC  GAAGAGGCAG  TCAACGGGGA  AACTCAGCAA  GCGCACTTAC      3180

AGGCGATTAA  AGAGCTGATA  GCGCGTGACA  AAAACCACCC  AAGCGTGGTG  ATGTGGAGTA      3240

TTGCCAACGA  ACCGGATACC  CGTCCGCAAG  GTGCACGGGA  ATATTTCGCG  CCACTGGCGG      3300

AAGCAACGCG  TAAACTCGAC  CCGACGCGTC  CGATCACCTG  CGTCAATGTA  ATGTTCTGCG      3360

ACGCTCACAC  CGATACCATC  AGCGATCTCT  TTGATGTGCT  GTGCCTGAAC  CGTTATTACG      3420

GATGGTATGT  CCAAAGCGGC  GATTTGGAAA  CGGCAGAGAA  GGTACTGGAA  AAAGAACTTC      3480

TGGCCTGGCA  GGAGAAACTG  CATCAGCCGA  TTATCATCAC  CGAATACGGC  GTGGATACGT      3540

TAGCCGGGCT  GCACTCAATG  TACACCGACA  TGTGGAGTGA  AGAGTATCAG  TGTGCATGGC      3600

TGGATATGTA  TCACCGCGTC  TTTGATCGCG  TCAGCGCCGT  CGTCGGTGAA  CAGGTATGGA      3660

ATTTCGCCGA  TTTTGCGACC  TCGCAAGGCA  TATTGCGCGT  TGGCGGTAAC  AAGAAAGGGA      3720

TCTTCACTCG  CGACCGCAAA  CCGAAGTCGG  CGGCTTTTCT  GCTGCAAAAA  CGCTGGACTG      3780

GCATGAACTT  CGGTGAAAAA  CCGCAGCAGG  GAGGCAAACA  ATGA                        3824
```

( 2 ) INFORMATION FOR SEQ ID NO:20:

( i ) SEQUENCE CHARACTERISTICS:
     ( A ) LENGTH: 382 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:20:

```
GTGACTCTTC  ATTTCTATTT  TCAGGATAAG  TTTGTGGTTT  GATGATCCCT  TGTTTCTAAG       60

TCTCTTGATT  TGTGAACAAT  TCAGGGTTTT  TATATATCTG  TATCTGTATT  TCTGAGTTGG      120

GTTGAGTTAT  TGGCTTCATG  CTGACTAAAC  ATGTTTGGCC  CTGTGTGTTC  TTCGAATTTC      180

ATTTTAATTG  CTTGATGGGT  TTTATTGACT  TGAGTAAAAG  TGTACTACTT  TATAGGTTTT      240

AAAAGAGTTT  TACTTTTGGT  GATTTTCCAA  TGGCTTTGAA  GAGAGAGATT  TAAATCATGG      300

GGTTACTATG  TTCTCATACT  GCGTTTGCTC  TGTTCTGTTG  TTTTTCTTTC  AGTTGATTGA      360

AACCTTGATT  GATCGGTCTA  GA                                                  382
```

( 2 ) INFORMATION FOR SEQ ID NO:21:

( i ) SEQUENCE CHARACTERISTICS:

-continued (A) LENGTH: 328 base pairs
(B) TYPE: nucleic acid
(C) STRANDEDNESS: single
(D) TOPOLOGY: linear (xi) SEQUENCE DESCRIPTION: SEQ ID NO:21:

```
ATGGTTATTG  CGGTGGCGAC  GACGAGCTCC  ATTGTTTCCG  GAATCAAGCT  TTCAGGGATC   60
TTAACTTCGT  TCAACGCCGT  AGATGATGCG  TCCAGTAGTT  GCGGAAGAAG  CAACTTGACC  120
GGAGTTAGAA  TTTTTCCGAC  ATTGAGTCGG  CGACGATTCT  CATCGATCGG  AGCTGTTTCC  180
CCAATTCGTG  GGGATGCTCA  ATCTTCCTTT  AGTCGCAGGT  AAAGCCTCGA  TTTTTGGGTT  240
TAGGTGTCTG  CTTATTAGAG  TAAAAACACA  TCCTTTGAAA  TTGTTTGTGG  TCATTTGATT  300
GTGCTCTTGA  TCCATTGAAT  TGCTGCAG                                        328
```